US008562658B2

(12) United States Patent
Shoham et al.

(10) Patent No.: US 8,562,658 B2
(45) Date of Patent: Oct. 22, 2013

(54) METHOD AND SYSTEM FOR OPTICAL STIMULATION OF NEURONS

(75) Inventors: Shy Shoham, Haifa (IL); Nairouz Farah, Nazareth (IL); Lior Golan, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 470 days.

(21) Appl. No.: 12/746,525

(22) PCT Filed: Dec. 4, 2008

(86) PCT No.: PCT/IL2008/001574
§ 371 (c)(1), (2), (4) Date: Jun. 6, 2010

(87) PCT Pub. No.: WO2009/072123
PCT Pub. Date: Jun. 11, 2009

(65) Prior Publication Data

US 2010/0262212 A1 Oct. 14, 2010

Related U.S. Application Data

(60) Provisional application No. 61/089,713, filed on Aug. 18, 2008, provisional application No. 60/992,921, filed on Dec. 6, 2007.

(51) Int. Cl.
*A61N 5/06* (2006.01)

(52) U.S. Cl.
USPC .............................................. 607/88; 607/89

(58) Field of Classification Search
USPC ................ 607/88, 89, 96, 100; 606/2, 27, 33
See application file for complete search history.

(56) References Cited

U.S. PATENT DOCUMENTS

| | | | | |
|---|---|---|---|---|
| 3,900,034 | A * | 8/1975 | Katz et al. | 607/89 |
| 5,497,254 | A * | 3/1996 | Amako et al. | 349/74 |
| 2003/0208245 | A1 | 11/2003 | Mahadevan-Jansen et al. | |
| 2009/0069871 | A1 | 3/2009 | Mahadevan-Jansen et al. | |
| 2011/0004272 | A1* | 1/2011 | Seibel et al. | 607/54 |
| 2012/0179228 | A1* | 7/2012 | DeCharms | 607/89 |

FOREIGN PATENT DOCUMENTS

| | | |
|---|---|---|
| WO | WO 2006/055582 | 5/2006 |
| WO | WO 2009/072123 | 6/2009 |

OTHER PUBLICATIONS

Wang et al. "All Optical Interti~ce tbr Parallel, Remote, and Spatiotemporal Control of Neuronal Activity", NANO Letters, XP007908648, 7(12): 3859-3863, Nov. 23, 2007. Abstract, Fig.1.*
International Search Report Dated Jun. 10, 2009 From the International Searching Authority Re.: Application No. PCT/IL2008/001574.
Written Opinion Dated Jun. 10, 2009 From the International Searching Authority Re.: Application No. PCT/IL2008/001574.

(Continued)

*Primary Examiner* — Armando Rodriguez

(57) ABSTRACT

A method of stimulating neurons present in a living body is disclosed. The method comprises directing light to an artificial light absorbing medium implanted extracellularly at a target location having the neurons therein, wherein wavelengths and intensities of the light are selected so as to heat the light absorbing medium by light absorption. The heating is sufficient to stimulate neurons nearby the light absorbing medium. In some embodiments, the light is spatially modulating so as to encode a stimulation pattern therein.

45 Claims, 18 Drawing Sheets

(56) References Cited

OTHER PUBLICATIONS

Aravanis et al. "An Optical Neural Interface: In Vivo Control of Rodent Motor Cortex With Integrated Fiberoptic and Optogenetic Technology", Journal of Neural Engineering, XP020123750, 4(3): S143-S156, Sep. 1, 2007.

Dufresne et al. "Computer-Generated Holographic Optical Tweezer Arrays", p. 1-8, Aug. 28, 2000.

Farah et al. "Patterned Optical Activation of Retinal Ganglion Cells", Proceedings of the 29th Annual International Conference of the IEEE Engineering in Medicine and Biology Society (EMBS) 2007, Cité Internationale, Lyon, France, August 23-26, 2007, XP031150969, p. 6368-6370, Aug. 1, 2007.

Lutz et al. "Holographic Photolysis of Caged Neurotransmitters", Nature Methods, 5(9): 821-827, Sep. 2008.

Pappas et al. "Nanoscale Engineering of a Cellular Interface With Semiconductor Nanoparticle Films for Photoelectric Stimulation of Neurons", Nano Letters, 792): 513-519, 2007.

Polin et al. "Optimized Holographic Optical Traps", Optics Express, 13(15): 5831-5845, Jul. 25, 2005.

Wang et al. "All Optical Interface for Parallel, Remote, and Spatiotemporal Control of Neuronal Activity", NANO Letters, XP007908648, 7(12): 3859-3863, Nov. 23, 2007. Abstract, Fig.1.

Wells et al. "Biophysical Mechanisms of Transient Optical Stimulation of Peripheral Nerve", Biophysical Journal, XP002529607, 93(7): 2567-2580, Oct. 1, 2007. Abstract, Fig.1.

International Preliminary Report on Patentability Dated Jun. 17, 2010 From the International Bureau of WIPO Re. Application No. PCT/IL2008/001574.

Di Leonardo et al. "Computer Generation of Optimal Holograms for Optical Trap Arrays", Optics Express, 15(4): 1913-1922, Feb. 19, 2007.

* cited by examiner

METHOD AND SYSTEM FOR OPTICAL STIMULATION OF NEURONS

RELATED APPLICATIONS

This application is a National Phase of PCT Patent Application No. PCT/IL2008/001574 having International filing date of Dec. 4, 2008, which claims the benefit of U.S. Provisional Patent Application Nos. 61/089,713 filed on Aug. 18, 2008 and 60/992,921 filed on Dec. 6, 2007. The contents of the above applications are all incorporated herein by reference.

FIELD AND BACKGROUND OF THE INVENTION

The present invention, in some embodiments thereof, relates to neuron stimulation and, more particularly, but not exclusively, to light induced neuron stimulation.

A neuroprosthesis is a device which is designed for replacing or improving the function of an impaired nervous system or sensory organ. Known in the art are neuroprosthesis for the treatment of functional disorders of the visual system, hearing system, cranial nerve system, spinal cord and peripheral nervous system [to this end see, e.g., International Patent Publication Nos. 98/036793 and WO 98/036795, and U.S. Pat. Nos. 6,393,327, 6,497,699, 6,829,510 and 7,447,548].

A visual prosthesis, for example, is a device that captures aspects of the visual environment and uses this information to stimulate nerves within the visual pathway to influence vision. A visual prosthesis may be placed within the eye or at some location on the path toward or within the visual part of the brain. Visual prosthetic devices within the eye can be positioned on the inner surface of the retina (i.e., epi-retinal) or under the retina (sub-retinal).

An auditory prosthesis is a device that delivers stimuli representative of sound to the spiral ganglion which is responsible for transmitting impulses from the inner ear to the brain. Also known are auditory prostheses that deliver stimuli directly to the auditory cortex or the auditory brainstem.

A neuroprosthesis operates by interacting with neurons. A neuron consists of: a branched pattern of processes, commonly known as dendrites, which act to receive information; a cell body, known as the soma, from which the dendrites extend, and which integrates the received information and provides for the metabolic needs of the neuron; and an axon extending from the soma, for transporting constituents between the soma and distant synapses, which transfer information to the next set of nerve dendrites.

When no stimulation is presented, the neuron is negatively polarized inside the soma membrane with respect to the outside of the membrane. Depolarization of a soma membrane creates an action potential, which effectively travels via axons, e.g., to the inner brain, thereby sending the stimulation signal thereto. Thus, information is represented in the nervous system as a series of action potentials that travel between the neurons via the membranes of axons.

Once stimulated, the neuron generates and allows propagation of an electrical impulse therein. Various techniques have been utilized for stimulating neurons. These include electrical stimulation, mechanical stimulation, thermal stimulation, chemical stimulation and optical stimulation. In the field of neuroprosthesis, the most common stimulation technique is electrical stimulation wherein a transient current or voltage pulse is applied via electrodes. For example, many visual prostheses include epi-retinal or sub-retinal microelectrode array implants, manufactured using micro-fabrication technology borrowed from the semiconductor industry.

Published Application No. 20030208245 discloses a technique for directly stimulating neural tissue with optical energy. An optical field having a wavelength of 1-6 μm is focused on a target neural tissue such that the target neural tissue propagates an electrical impulse. The focusing is onto an area of 50-600 μm micrometers.

U.S. Published Application No. 20060161227 discloses a system for stimulating auditory neurons associated with the spiral ganglion cells. Optical energy at a wavelength of 0.5-10 μm is delivered along an optical path to a target site of auditory neurons to evoke compound action potential therein. The evoked action potential is monitored by monitoring means.

The light sources used in the above publications are laser devices, and the produced optical energy is absorbed by the tissue's water content within a typical absorption distance of several hundred microns, allowing the optical field to directly interact with the tissue. It has been hypothesized [Wells et al., "Biophysical mechanisms of transient optical stimulation of peripheral nerve," Biophys J 93, 2567-80 (2007)] that the photobiological effect of light absorption on the tissue is mediated through a photo-thermal mechanism, rather than electrical field, photochemical or photomechanical mechanisms.

A system capable of patterned activation of many neurons with millisecond precision using rapid UV laser deflection has recently been disclosed [Shoham et al., "Rapid neurotransmitter uncaging in spatially defined patterns," Nature Methods 2, 837-843 (2005)]. In this system, UV light is used to activate neurons by uncaging glutamate, the major excitatory neurotransmitter in the central nervous system.

Recently, retinal ganglion cells have been directly activated by artificially causing them to express Channelrhodopsin II (ChR2), a light-gated cation channel [Reutsky et al., "Patterned optical activation of Channelrhodopsin II expressing retinal ganglion cells," in CNE '07. 3rd International IEEE/EMBS Conference on Neural Engineering, 2007 50-52 (2007)]. Patterned stimulation of the cells was demonstrated by means of video projection technology based on a Texas Instruments Digital Minor Device.

Additional background art includes Wells et al. "Optical stimulation of neural tissue in vivo," Opt Lett 30, 504-6 (2005); Pappas et al., "Nanoscale Engineering of a Cellular Interface with Semiconductor Nanoparticle Films for Photoelectric Stimulation of Neurons," Nano Letters (2007) Vol. 7, No. 2, 513-519 and Izzo et al., "Laser stimulation of the auditory nerve," Lasers Surg Med 38, 745-53 (2006); U.S. Published Application Nos. 20060161227 and 20030208245].

SUMMARY OF THE INVENTION

According to an aspect of some embodiments of the present invention there is provided a method of stimulating neurons present in a living body. The method comprises directing light to an artificial light absorbing medium implanted extracellularly at a target location having the neurons therein, wherein wavelengths and intensities of the light are selected so as to heat the light absorbing medium by light absorption, the heating being sufficient to stimulate neurons nearby the light absorbing medium.

According to some embodiments of the invention the method further comprises extracellularly implanting the artificial light absorbing medium at the target location.

According to some embodiments of the invention the light is directed so as to simultaneously form a stimulation pattern at the target location.

According to some embodiments of the invention the method further comprises spatially modulating the light so as to encode the stimulation pattern therein.

According to an aspect of some embodiments of the present invention there is provided a method of stimulating neurons. The method comprises: spatially modulating light so as to encode a stimulation pattern therein; and directing the light to a target location having the neurons therein so as to simultaneously form the stimulation pattern at the target location, wherein wavelengths and intensities forming the stimulation pattern are selected so as to selectively stimulate the neurons.

According to an aspect of some embodiments of the present invention there is provided a neurostimulation system. The neurostimulation system comprises: an artificial light absorbing medium implantable extracellularly in a living body at target location having therein a plurality of neurons; and an illumination system having a light source for generating light and optics for directing the light to the artificial light absorbing medium, wherein wavelengths and intensities of the light are selected so as to heat the light absorbing medium by light absorption, the heating being sufficient to stimulate neurons nearby the light absorbing medium.

According to some embodiments of the invention the illumination system comprises a projector system configured for generating a spatially modulated light beam encoded with a stimulation pattern.

According to an aspect of some embodiments of the present invention there is provided a neurostimulation device. The neurostimulation device comprises: a projector system for generating a spatially modulated light beam encoded with a stimulation pattern; and optics configured for directing the light to a target location having a plurality of neurons so as to simultaneously form the stimulation pattern at the target location; wherein wavelengths and intensities forming the stimulation pattern are selected so as to selectively stimulate the neurons.

According to an aspect of some embodiments of the present invention there is provided a neuroprosthesis system. The neuroprosthesis system comprises: the neurostimulation device described herein; and a sensing device for sensing information from the environment and transmitting signals pertaining to the information to the neurostimulation device; wherein the projector system is configured for calculating the stimulation pattern based on the information.

According to some embodiments of the invention the target location is implanted with an artificial light absorbing medium, and wherein the wavelengths and intensities are selected so as to heat the light absorbing medium by light absorption, the heating being sufficient to stimulate neurons nearby the light absorbing medium.

According to some embodiments of the invention the neurons express a light-activated ion channel protein, and wherein the wavelengths and intensities are selected so as to activate the light-activated ion channel protein.

According to some embodiments of the invention the method further comprises, transfecting the neurons by gene transfer vectors capable of inducing expression of the light-activated ion channel protein.

According to some embodiments of the invention the projector system comprises a spatial light modulator having a liquid crystal.

According to some embodiments of the invention the projector system is configured for providing phase-only modulation.

According to some embodiments of the invention the projector system is configured for providing concurrent phase and amplitude modulation.

According to some embodiments of the invention the optics is a free-space optics.

According to some embodiments of the invention the optics comprises an optical fiber bundle.

According to some embodiments of the invention the light absorbing medium is extracellularly distributed at the target location.

According to some embodiments of the invention the light absorbing medium comprises light absorbing particles.

According to some embodiments of the invention the light absorbing medium comprises a dye.

According to some embodiments of the invention the light absorbing particles are metallic nanoparticles.

According to some embodiments of the invention the light absorbing medium comprises a light absorbing film.

According to some embodiments of the invention the stimulation pattern is a three-dimensional stimulation pattern.

According to some embodiments of the invention the light is selected so as to generate non-linear optical effects.

According to some embodiments of the invention the light is characterized by a pulse width which is shorter that one picosecond.

According to some embodiments of the invention the target location is a retina.

According to some embodiments of the invention the target location is a cochlea.

According to some embodiments of the invention the target location is in the cerebral cortex.

According to some embodiments of the invention the target location is in the brainstem.

According to some embodiments of the invention the target location is the vagus nerve.

According to some embodiments of the invention the target location is a cranial nerve.

According to some embodiments of the invention the target location is a neuron culture.

According to some embodiments of the invention the modulated light beam is dynamically encoded with an alternating sequence of pseudo-random frames forming together a symmetric stimulation pattern at the target location.

According to some embodiments of the invention the intensities are selected so as to reduce efficiency inhomogeneities within the stimulation pattern.

According to some embodiments of the invention the intensities are inversely proportional to a square of a sinc function.

According to some embodiments of the invention the optics is characterized by a numerical aperture selected such that an elementary spot size of the stimulation pattern is at most 20 microns.

According to some embodiments of the invention the light is encoded in a time-multiplexed manner, wherein stimulation patterns transmitted at different times correspond to different light spectra.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram of a method suitable for stimulating neurons present in a living body, according to various exemplary embodiments of the present invention;

FIG. 2 is a flowchart diagram of another method suitable for stimulating neurons present in a living body, according to various exemplary embodiments of the present invention;

FIG. 3 is a flowchart diagram of an additional method suitable for stimulating neurons present in a living body, according to various exemplary embodiments of the present invention;

FIG. 4 is a flowchart diagram of a further method suitable for stimulating neurons present in a living body, according to various exemplary embodiments of the present invention;

Figure 6:
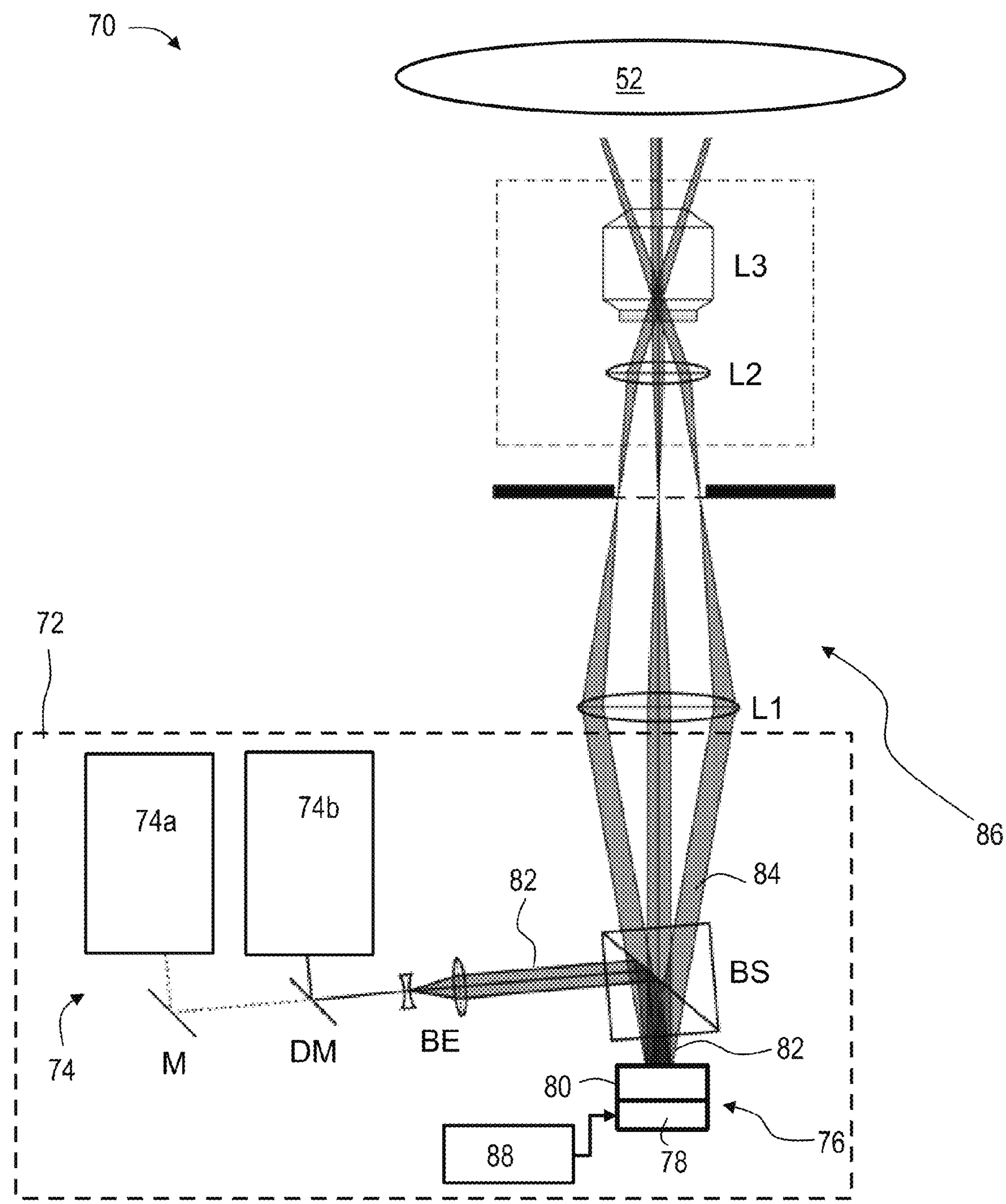
Figure 7:
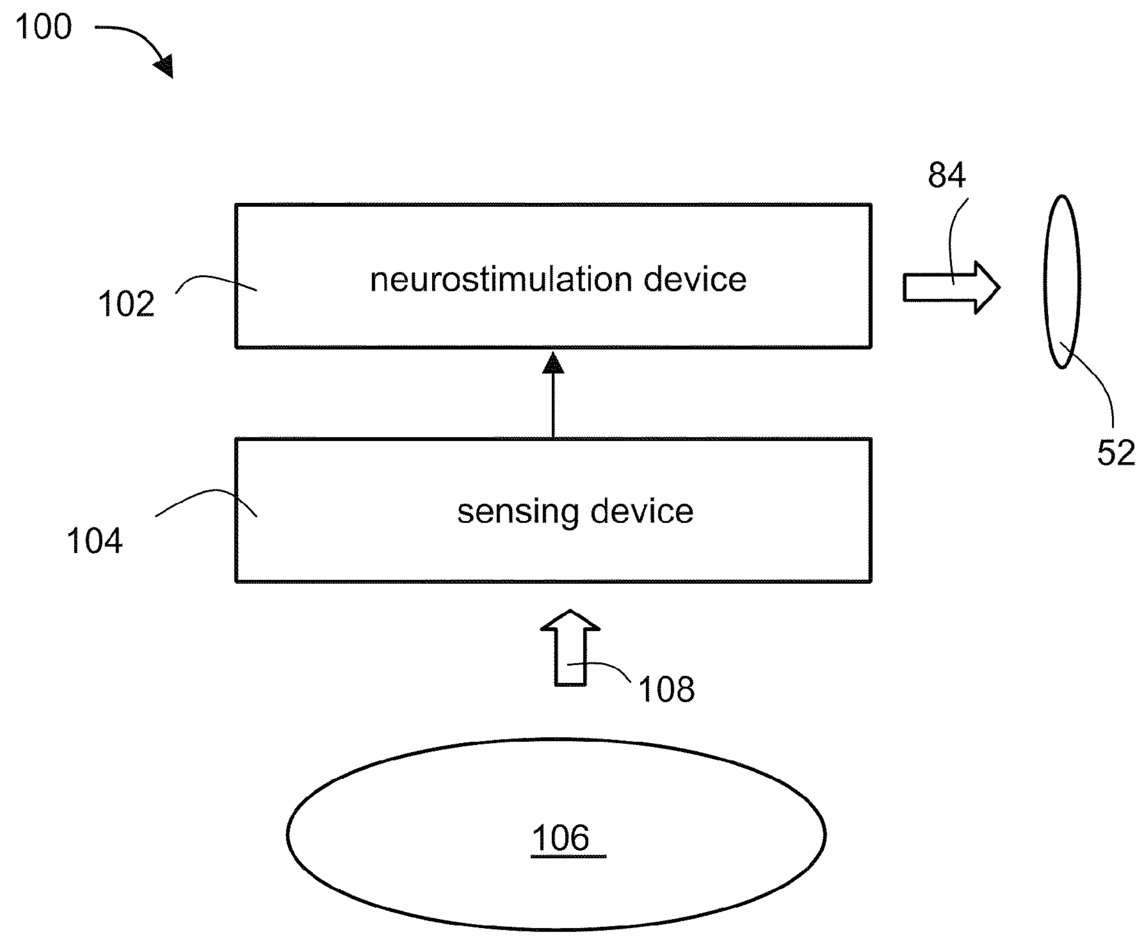
Figure 8A:
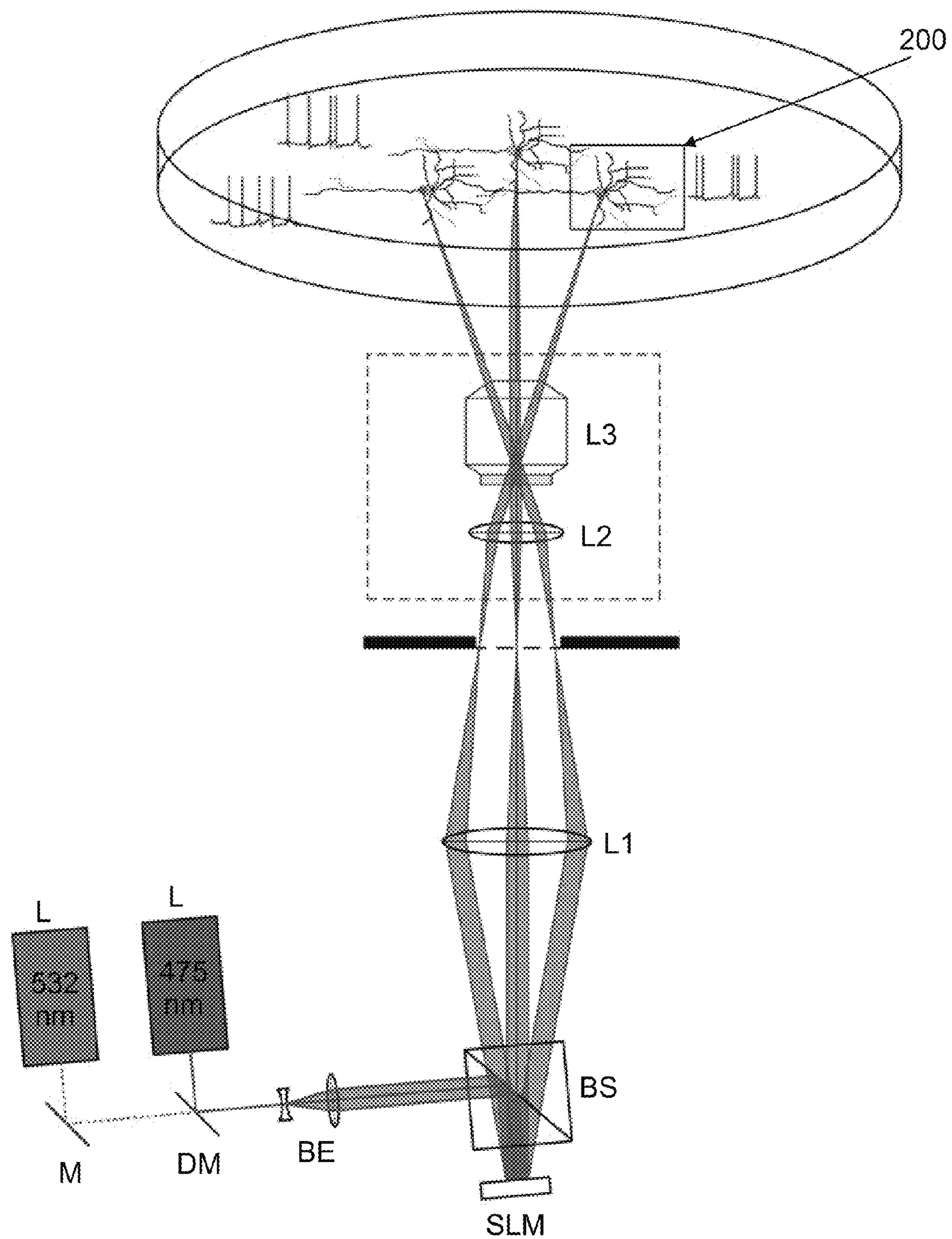
Figure 8B:
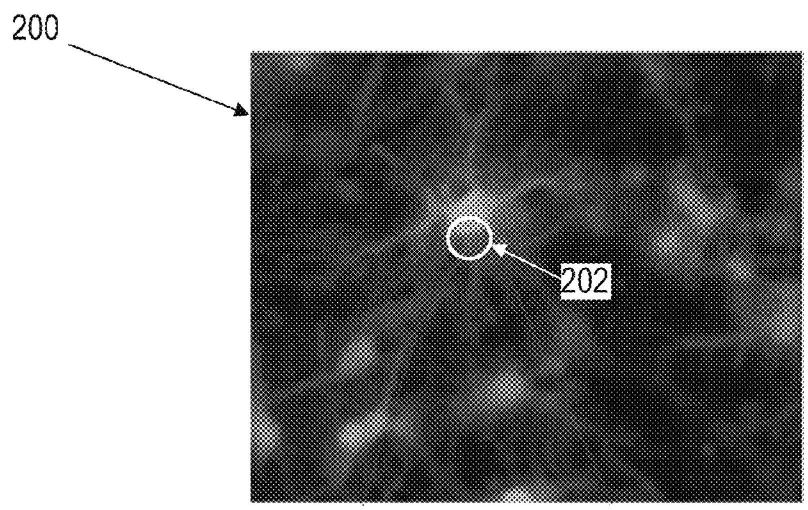
Figure 8C:
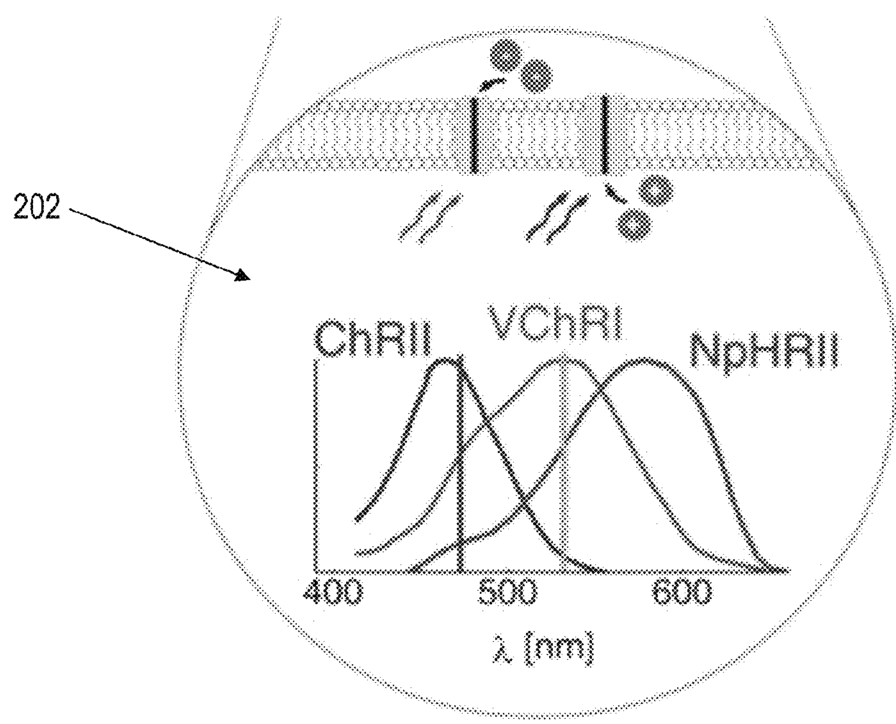
Figure 8D:
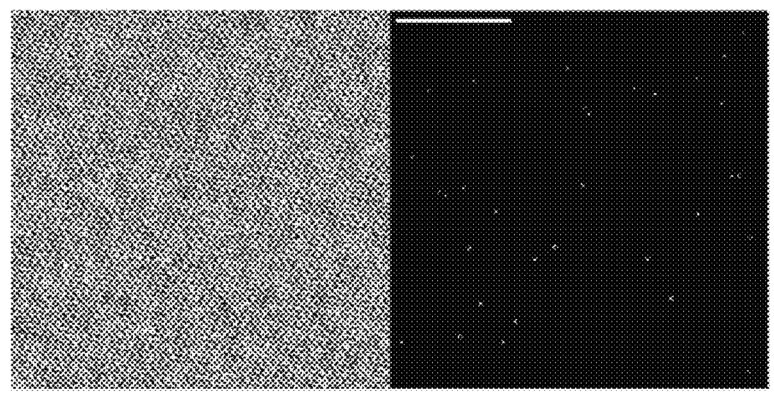
Figure 9B:
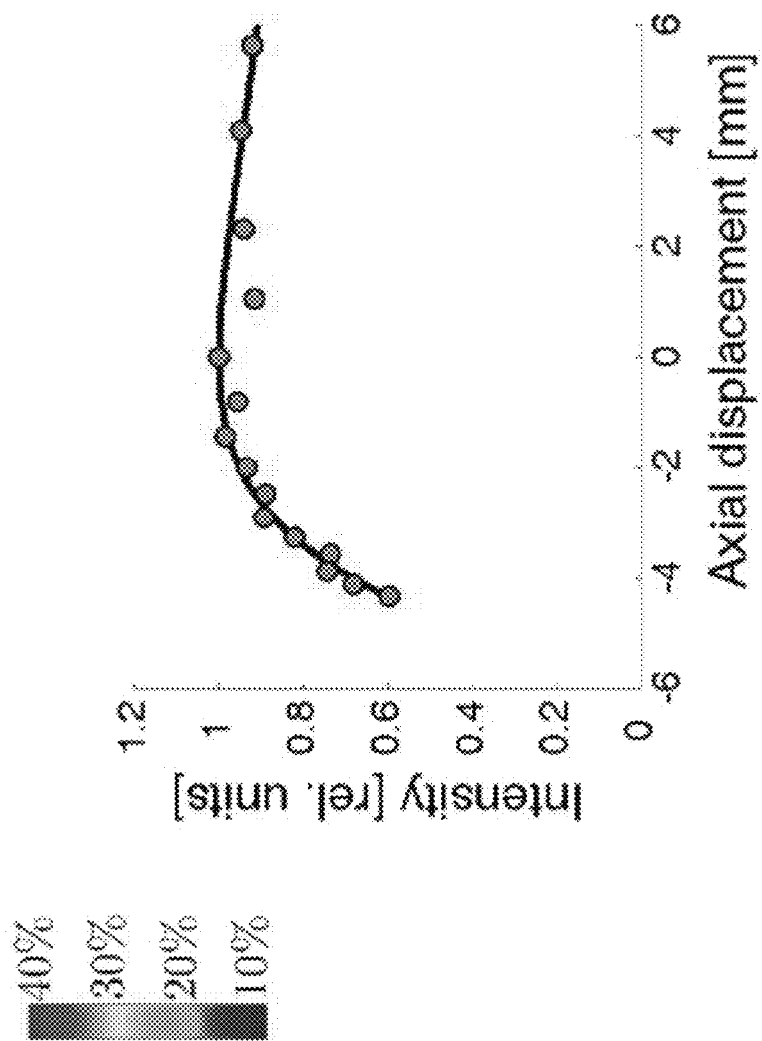
Figure 9A:
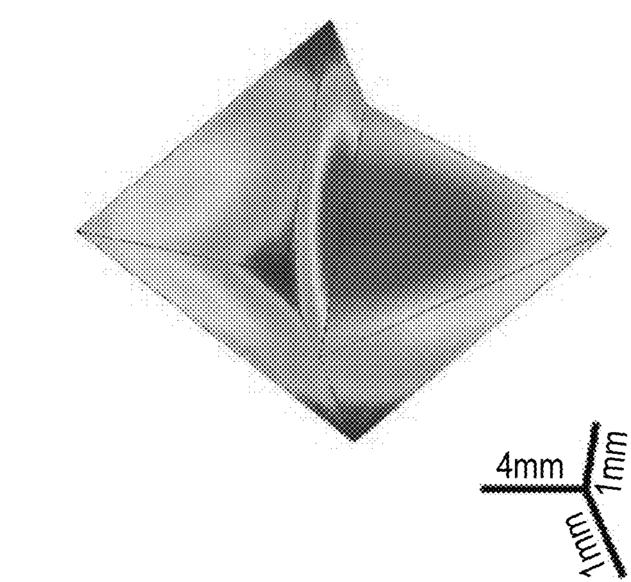
Figures 9C, 9D:
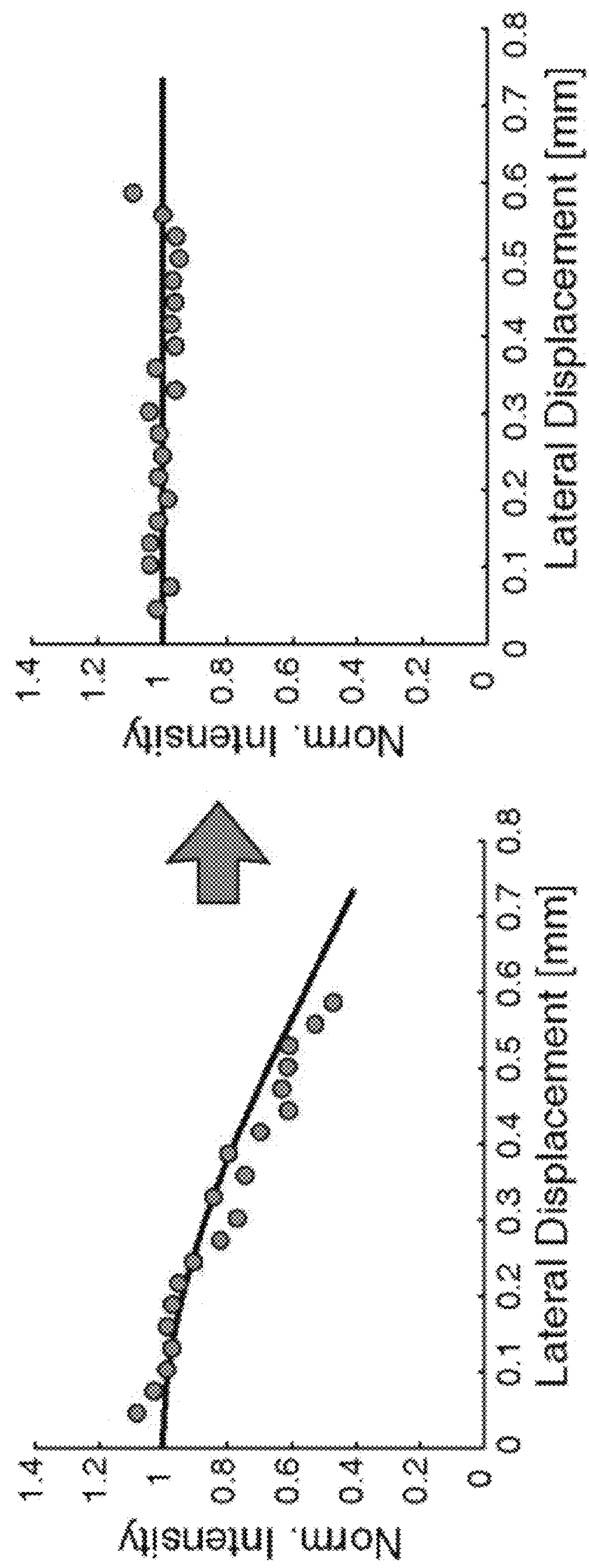
Figure 9F:
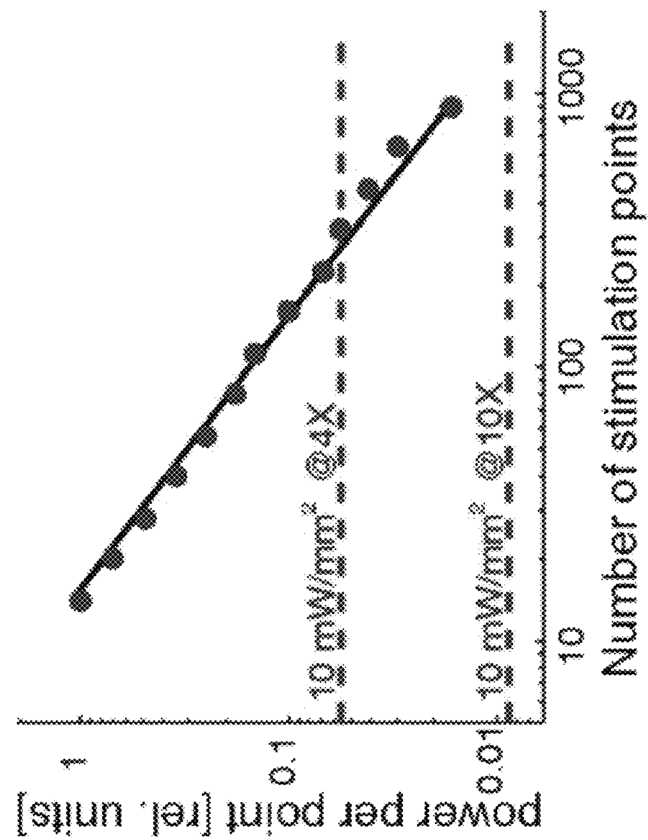
Figure 9E:
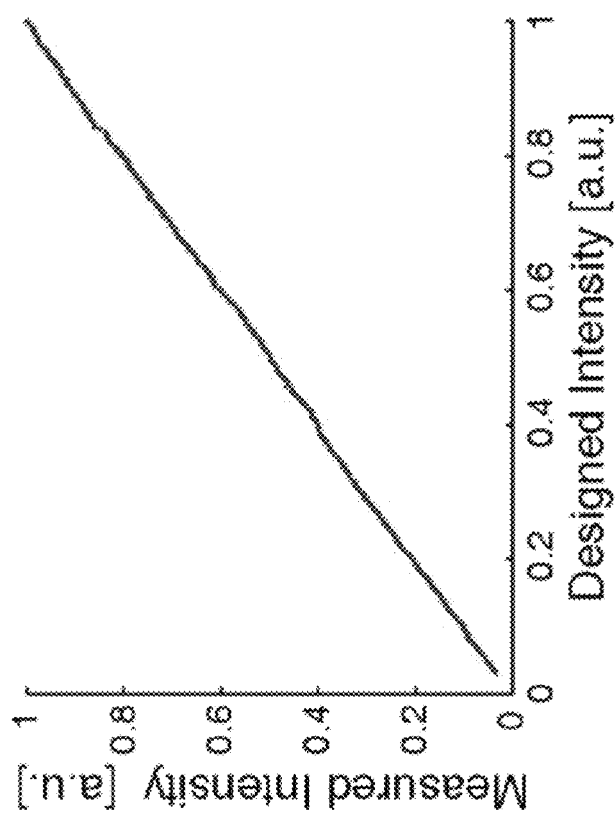
Figure 10A:
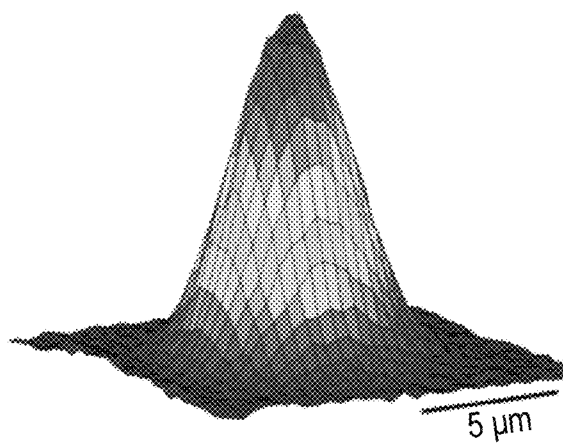
Figure 10B:
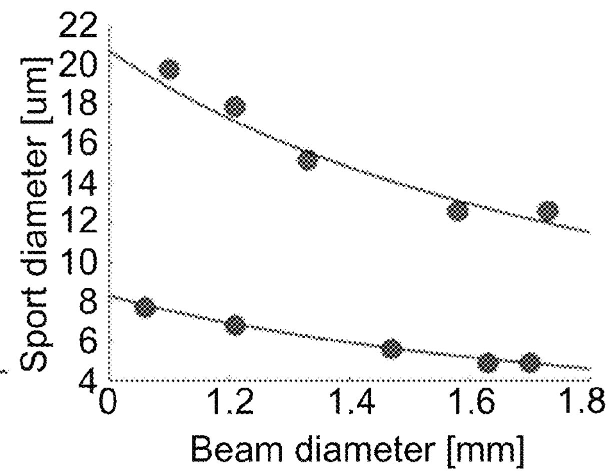
Figure 10C:
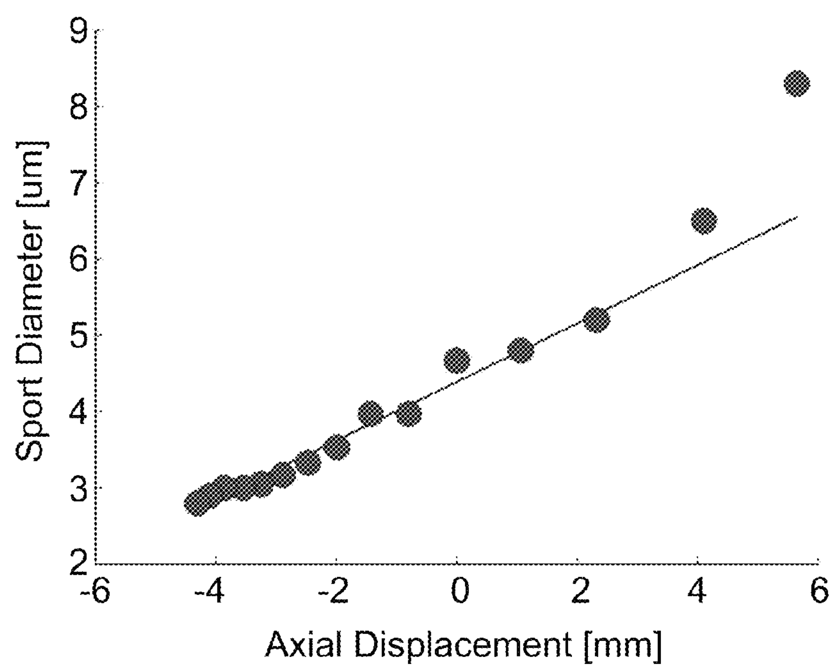
Figure 10D:
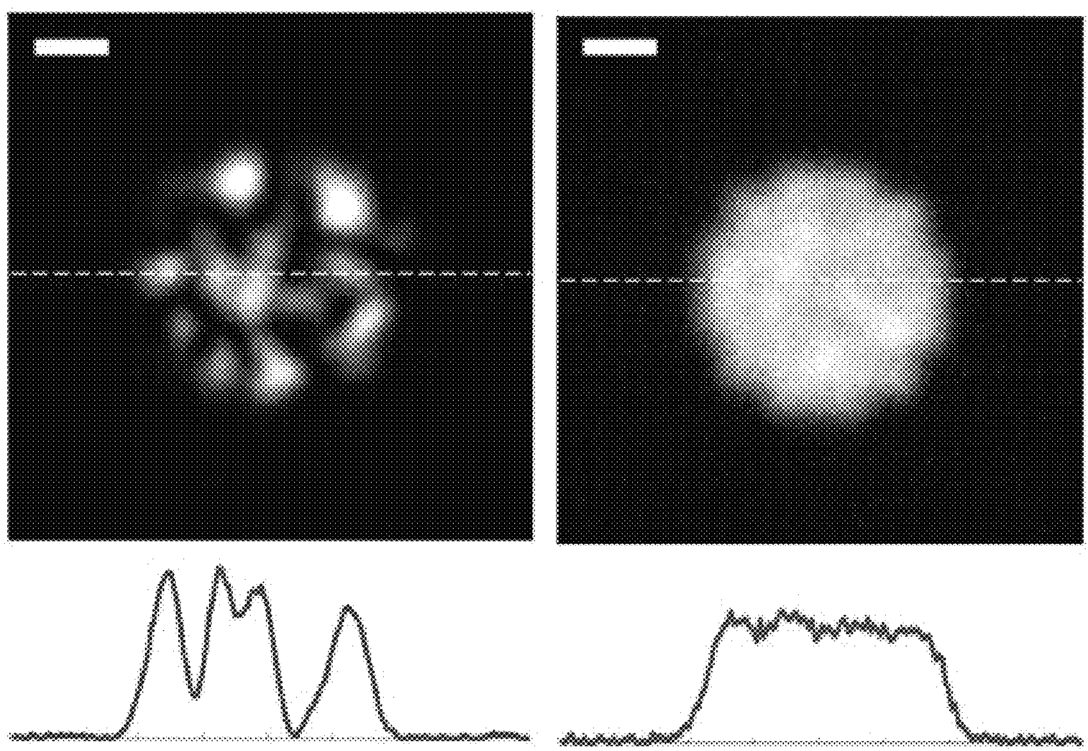
Figure 10E:
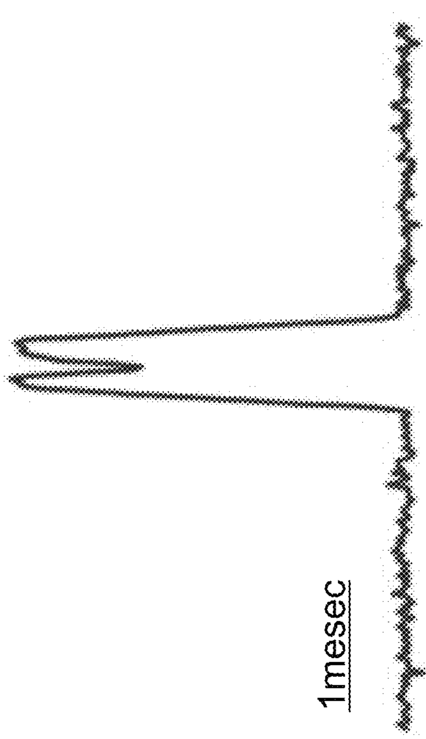
Figure 10F:
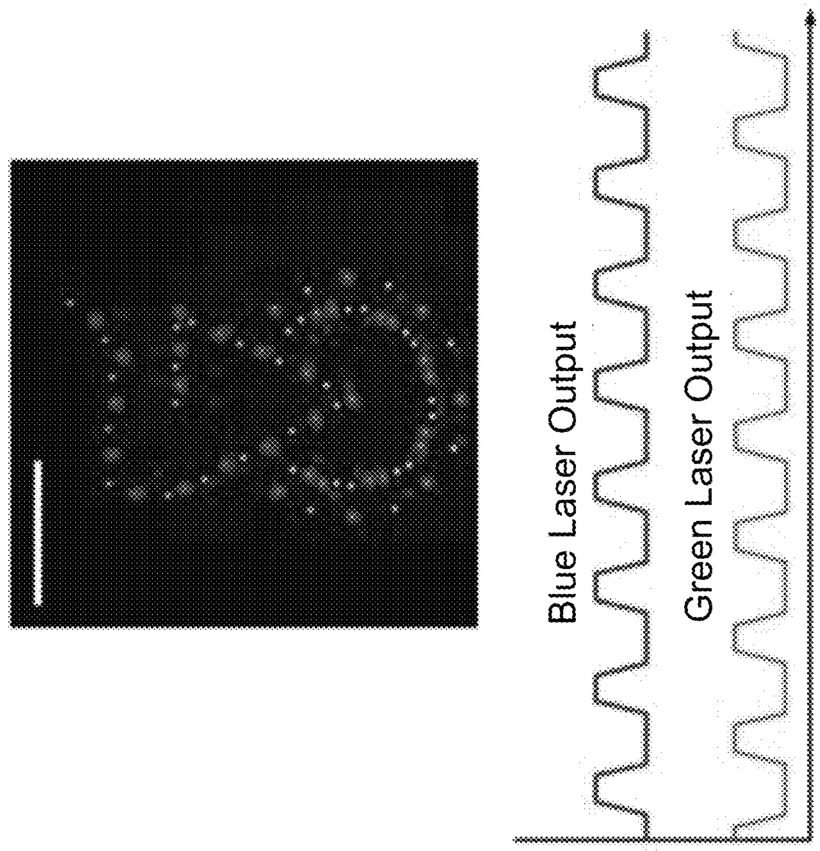
Figure 11A:
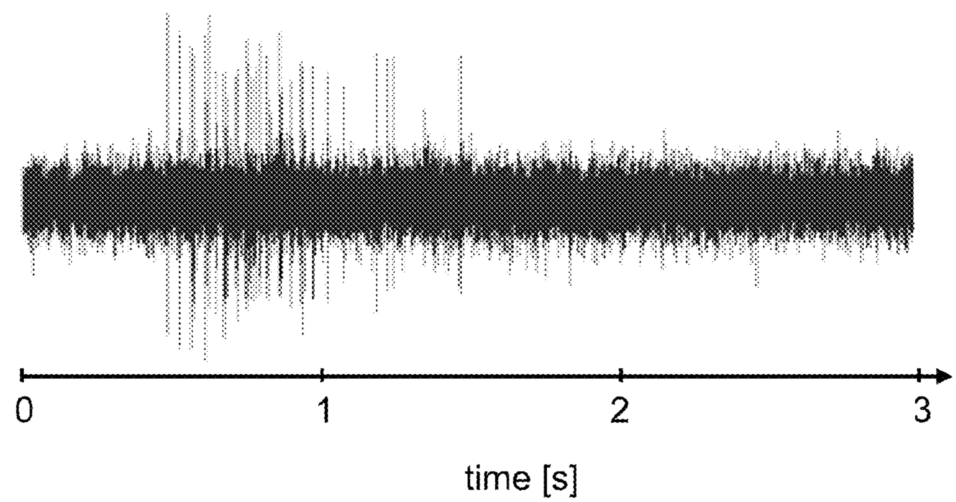
Figure 11B:
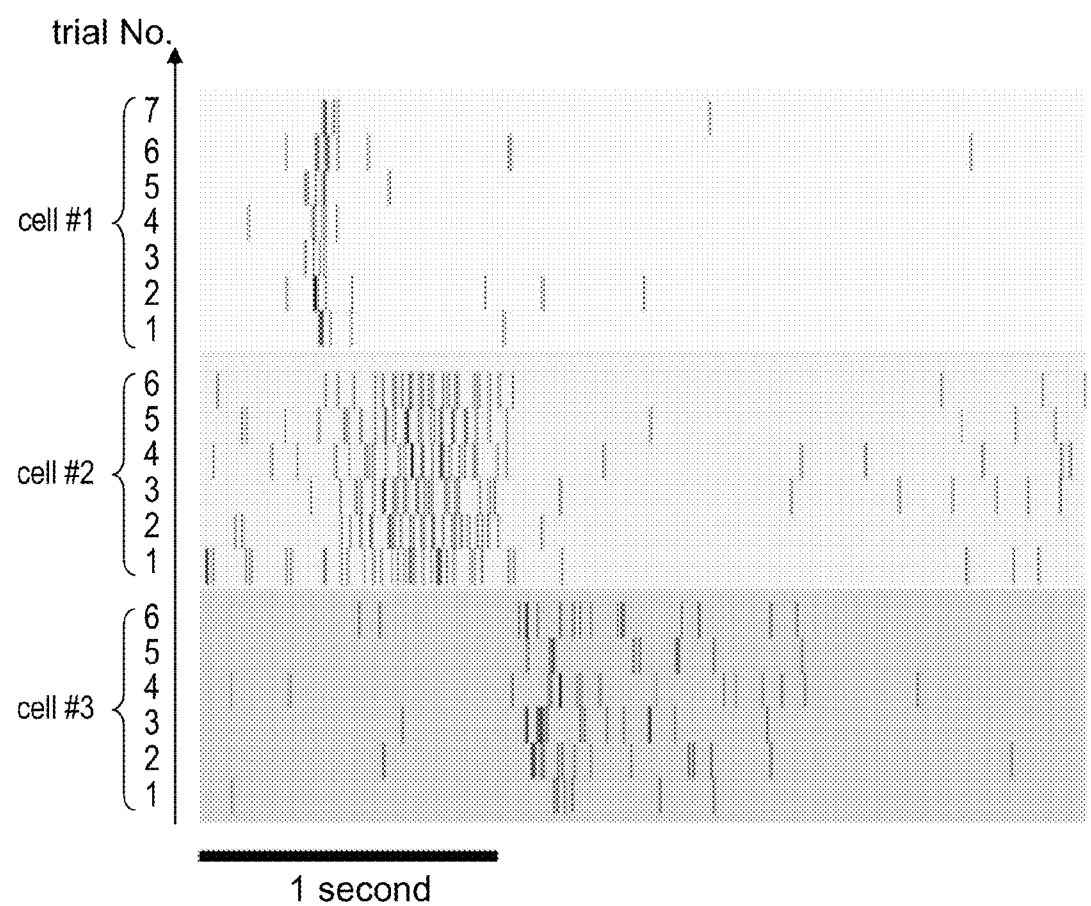
Figure 12A:
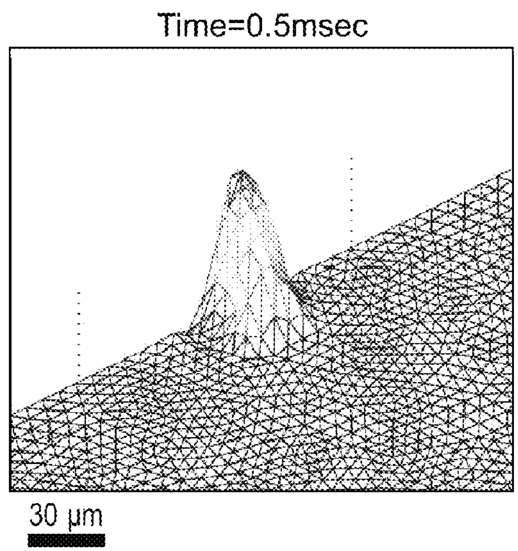
Figure 12B:
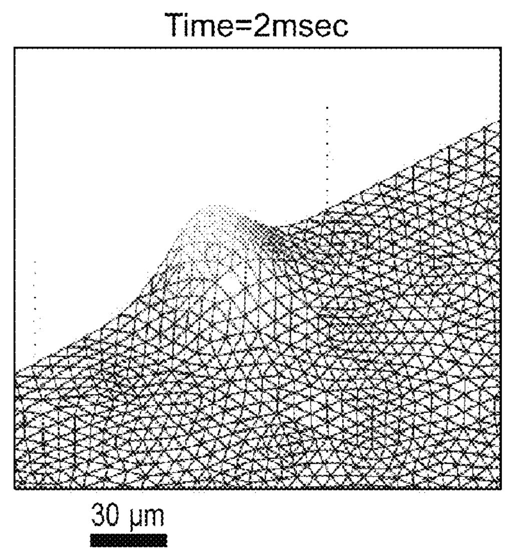
Figure 12C:
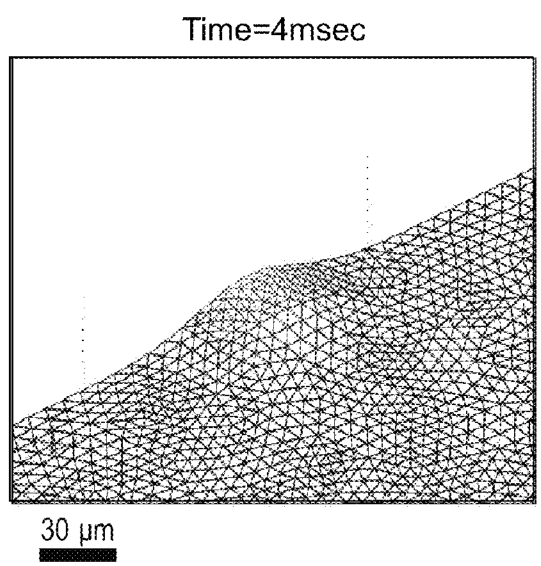
Figure 12D:
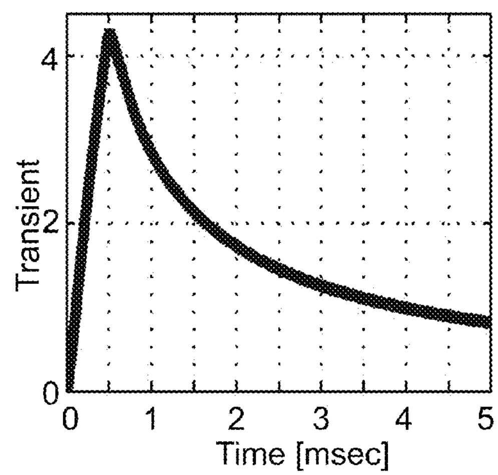

FIGS. 5A-E are schematic illustrations of a neurostimulation system, according to various exemplary embodiments of the present invention;

FIG. 6 is a schematic illustration a neurostimulation device, according to various exemplary embodiments of the present invention;

FIG. 7 is a schematic illustration of a neuroprosthesis system, according to various exemplary embodiments of the present invention;

FIGS. 8A-C are schematic illustrations of an experimental setup (FIG. 8A) and procedure (FIGS. 8B-C), utilized in experiments performed in accordance with some embodiments of the present invention;

FIG. 8D shows a phase image used in experiments, performed in accordance with some embodiments of the present invention, for generating a sparse pseudo-random pattern of photo-stimulation points;

FIGS. 9A-D shows theoretical and measured spatial distribution of efficiency, as predicted and measured in experiments performed in accordance with some embodiments of the present invention;

FIG. 9E shows intensities of individual stimulation shapes as controlled according to various exemplary embodiments of the present invention;

FIG. 9F shows average power density per stimulation shape, according to various exemplary embodiments of the present invention;

FIG. 10A is a three-dimensional plot of Gaussian stimulation shape according to various exemplary embodiments of the present invention;

FIGS. 10B-C demonstrate techniques for controlling the size of the stimulation shape;

FIG. 10D demonstrates techniques for reducing speckle, according to various exemplary embodiments of the present invention;

FIG. 10E show a characteristic stimulation pulse, according to various exemplary embodiments of the present invention;

FIG. 10F shows time sharing technique utilizing the shortness of the pulse of FIG. 10E, according to various exemplary embodiments of the present invention;

FIG. 11A shows raw data of a single neuron response, as measured in experiments performed in accordance with some embodiments of the present invention;

FIG. 11B shows responses of three different neurons as measured in experiments performed in accordance with some embodiments of the present invention; and FIGS. 12A-D show a spatial (FIGS. 12A-C) and temporal (FIG. 12D) thermal response profile, as obtained by computer simulations, performed in accordance with some embodiments of the present invention.

Figure 13:
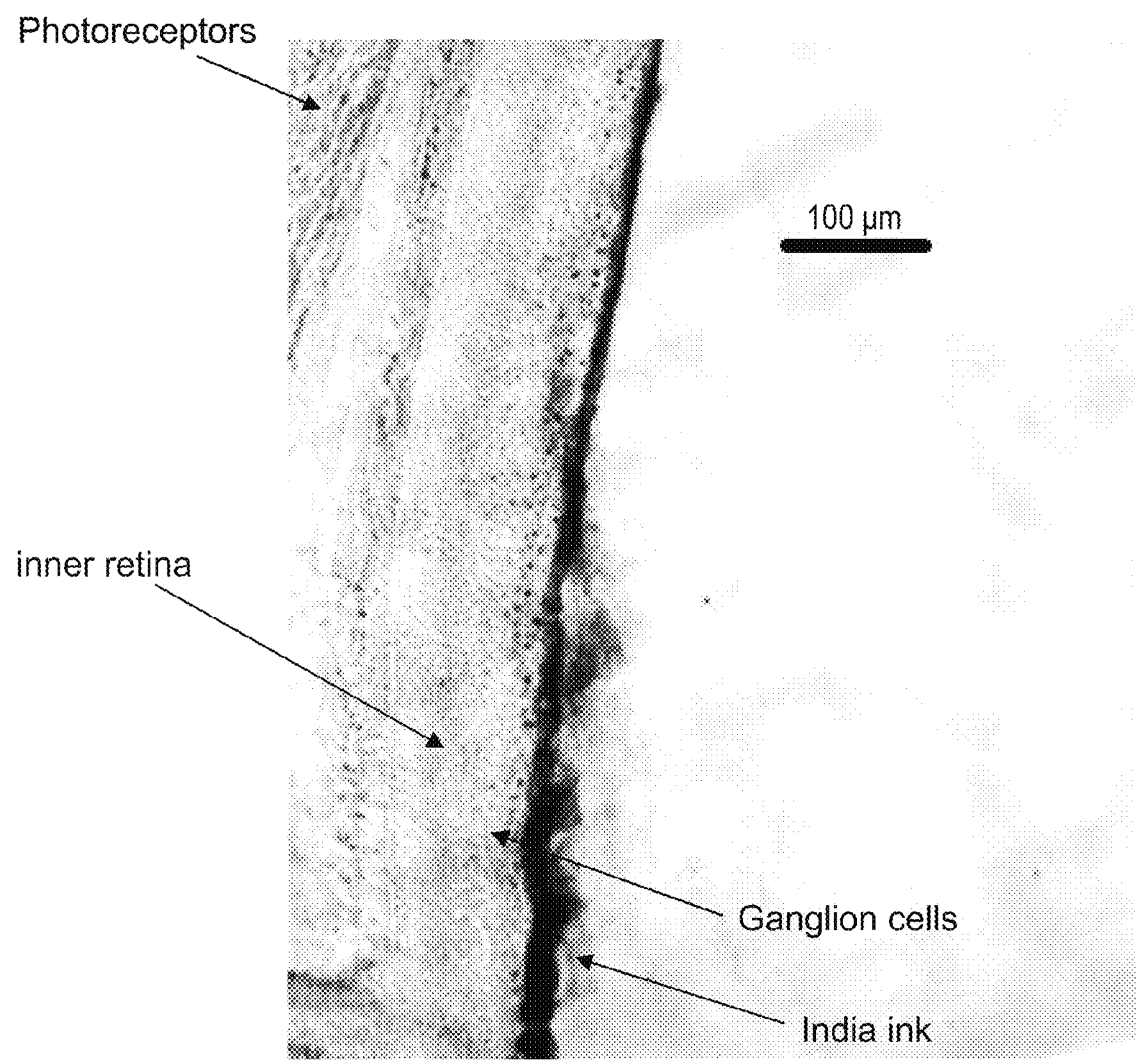

FIG. 13 is an image of a stained retina, according to some embodiments of the present invention.

DESCRIPTION OF SPECIFIC EMBODIMENTS OF THE INVENTION

The present invention, in some embodiments thereof, relates to neuron stimulation and, more particularly, but not exclusively, to light induced neuron stimulation.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Some embodiments of the present invention are directed to a method, device and system suitable for stimulating neurons present in a body of living subject, typically a mammalian subject, e.g., a human subject. In various exemplary embodiments of the invention the neurons are stimulated by optical energy delivered to a target location at which the neurons are present.

The target location can be any location in the living body in which there is a neural tissue containing a large population of neurons. In some embodiments of the present invention the target location is a retina of the subject, in which case the neurons to be stimulated can be, for example, the retinal ganglion cells. In some embodiments of the present invention the target location is part of the cochlea of the subject, in which case the neurons to be stimulated are the spiral ganglion cells. In some embodiments of the present invention the target location is part of the cerebral cortex of the subject's brain, preferably the visual cortex or the auditory cortex, but may also be or include other cortical regions such as, but not limited to, motor cortex, premotor cortex, supplementary motor cortex, somatosensory cortex, etc. In some embodiments of the present invention the target location is one or more of the brainstem structures (midbrain, pons, medulla) of the subject. In some embodiments of the present invention the target location is part of the Thalamus or the sub-Thalamic nucleus (STN). In some embodiments of the present invention the target location is a nerve in the peripheral nervous system, the autonomic nervous system or cranial nerve system, e.g.: the vagus nerve, the optic nerve, the auditory nerve, a motor nerve, or a sensory nerve. In some embodiments of the present invention the target location is part of the spinal cord of the subject. In some embodiments of the present invention the target location is part of the enteric nervous system.

The target location can also be an ex-vivo target location, such as, but not limited to, a neuron culture.

Referring now to the drawings, each of FIGS. 1-4 is a flowchart diagram of a method suitable for stimulating neurons present in a living body, according to various exemplary embodiments of the present invention.

It is to be understood that, unless otherwise defined, the operations described hereinbelow can be executed either contemporaneously or sequentially in many combinations or orders of execution. Specifically, the ordering of any of the flowchart diagrams in the drawings is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

Figure 1:
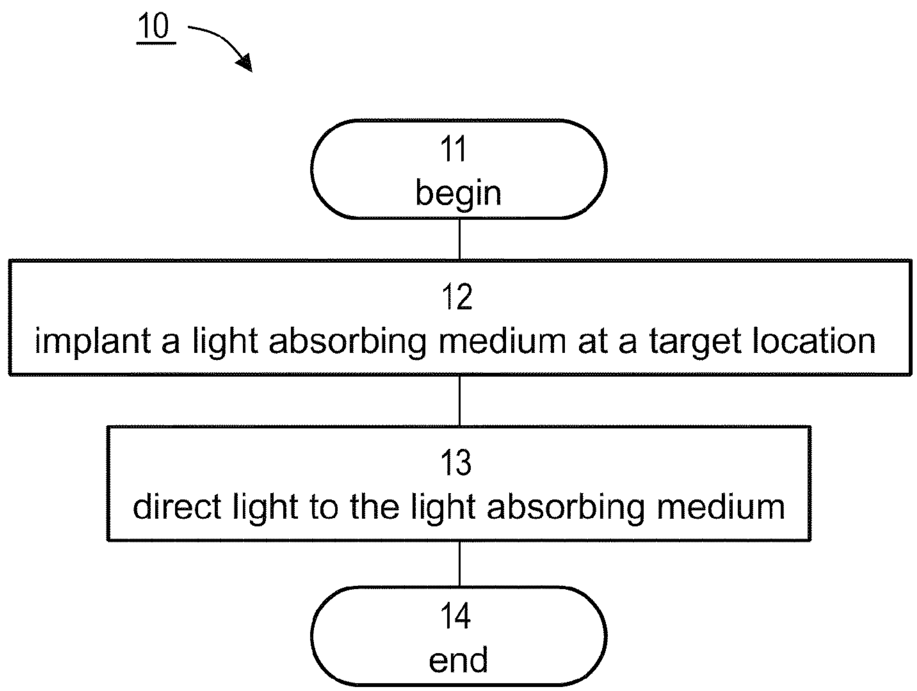

With specific reference to FIG. 1, the method, referred to hereinunder as method 10, begins at 11 and optionally and preferably continues to 12 at which a light absorbing medium is implanted in a target location having the neurons therein. Alternatively, the method can be executed after the light absorbing medium has been implanted in the target location.

The light absorbing medium can be in the form of a plurality of particles, such as biocompatible dyes or physiologically acceptable nanoparticles having sufficiently high light absorption coefficients in situ (preferably above 10 $mm^{-1}$, more preferably above 30 $mm^{-1}$, more preferably above 40 $mm^{-1}$, more preferably above 50 $mm^{-1}$ across a wavelength range spanning from IR to Violet or at specific absorption peaks within this range). Representative examples of such particles include, without limitation, various biocompatible inks (e.g., India ink, or any of the inks disclosed in U.S. Pat. No. 7,288,578 and U.S. Published Application No. 20080012164) and light-absorbing nanoparticles, for example, metallic (e.g., gold) nanoparticles.

The light absorbing medium can comprise a pigment or a dye. One group of pigments suitable for the present embodiments is the family of pigments used for Tattooing, which are known to be biocompatible. There are a number of Tattoo ink types which come in various colors. Black dyes include India ink, which is made from carbon particles. India ink has previously been used as an optical absorber in tissue-simulating phantoms. Other black inks are commonly made from powdered minerals and crystals, and amorphous carbon from combustion. Also contemplated are other colors, such as, but not limited to, brown inks, e.g., inks made from ion oxides and clay, red inks, e.g., inks are made from Naptha derivatives, orange and/or yellow inks, e.g., inks made from Monoazo and Diazo synthetic pigments, purples inks, e.g., inks made from Dioxazine, blue and/or green inks, e.g., inks made from copper Pthyocalanine.

The light absorbing medium can comprise nanoparticles, such as, but not limited to, gold and/or silver and/or titanium oxide nanoparticles which are highly absorbing in the visible range. The peak absorption around 530 nm of 10 nm gold particles is red-shifted when the size of the particles becomes larger. The light absorbing medium can also comprise nanorods, e.g., gold nanorods which are rod-shaped gold nanoparticles whose aspect ratios tune the surface plasmon resonance (SPR) band from the visible to near infrared wavelength. The use of nanorods is advantageous because near infrared light transmits readily through human skin and tissue.

The light absorbing medium can also comprise a biological material. One type of biological light absorbing medium is melanin, which is a heterogeneous, complex polymer that is synthesized in specialized organelles (melanosomes) of the epidermal melanocytes and then transferred to surrounding keratinocytes. The melanin absorbs light across the entire visible range and into the near-IR. Another family of biological light absorbing medium are porphyrins, which are composed of a deeply colored heterocyclic macrocycle characterized by the presence of four pyrroline subunits interconnected via their $\alpha$ carbon atoms via methine bridges (for example: heme and chlorophyll). Another type of biological light absorbing medium is retinoids, which is a chemical compound that is chemically related to vitamin A. Representative examples of retinoids suitable for the present embodiment, include, without limitation, retinal and beta-carotene. Another type of biological light absorbing medium is bacteriorhodopsin, which absorbs light at a wavelength range of 500-650 nm (absorption maximum at 568 nm).

Other types of light absorbing media are colorants that are presently widely used in various food, drugs and cosmetics (FD&C) applications. The colorants can optionally be encapsulated in a sol jel matrix for prolonging their presence in the target location. Such encapsulation technique is known in the art, see, e.g., International Patent Application Nos. WO01/80823 and WO04/081222. A review of sol jel technique is found in Avnir et al., in The Chemistry of Organosilicon Compounds, Vol. 2 (1998), Chapter 48 Page 192.

Representative examples of water-soluble colorants that are usable in this and other aspects of the present invention include, without limitation, FD&C colors such as EXT.D&C Green No. 1, EXT.D&C Yellow No. 7, EXT.D&C Yellow No. 1, EXT. D&C Orange No. 3, FD&C Red No. 4, D&C Orange No. 4, FD&C Yellow No. 6, D&C Red No. 2, D&C Red No. 33, EXT.D&C Yellow No. 3, FD&C Yellow No. 5, D&C Brown No. 1, D&C Black No. 1, FD&C Green No. 3, FD&C Blue No. 1, D&C Blue No. 4, D&C Red No. 19, D&C Red No. 37, EXT. D&C Red No. 3, D&C Yellow No. 8, D&C Orange No. 5, D&C Red No. 21, D&C Red No. 22, D&C Red No. 28, D&C Red No. 27, D&C Orange No. 10, D&C Orange No. 11, FD&C Red No. 3, D&C Yellow No. 11, D&C Yellow No. 10, D&C Green No. 8, EXT. D&C Violet No. 2, D&C Green No. 5 and FD&C Blue No. 2.

A list of additional water-soluble colorants usable in the context of the present embodiments, according to their Color Index No. and name, their Japanese name and their FDA name is set forth in Table 1 below.

TABLE 1

| CI No. | Japanese name | FDA name | Color Index name |
|---|---|---|---|
| C.I.10020 | Green No. 401 | (EXT. D & C Green No. 1) | Acid Green 1 |
| C.I.10316 | Yellow No. 403-1 | (EXT. D & C Yellow No. 7) | Acid Yellow 1 |
| C.I.13065 | Yellow No. 406 | (EXT. D & C Yellow No. 1) | Acid Yellow 36 |
| C.I.14600 | Orange No. 402 | (EXT. D & C Orange No. 3) | Acid Orange 20 |
| C.I.14700 | Red No. 504 | FD & C Red No. 4 | Food Red 1 |
| C.I.15510 | Orange No. 205 | D & C Orange No. 4 | Acid Orange 7 |
| C.I.15620 | Red No. 506 | | Acid Red 88 |
| C.I.15985 | Yellow No. 5 | FD & C Yellow No. 6 | Food Yellow 3 |
| C.I.16150 | Red No. 503 | | Acid Red 26 |
| C.I.16155 | Red No. 502 | | Food Red 6 |
| C.I.16185 | Red No. 2 | (D & C Red No. 2) | Acid Red 27 |
| C.I.16255 | Red No. 102 | | Acid Red 18 |
| C.I.17200 | Red No. 227 | D & C Red No. 33 | Acid Red 33 |
| C.I.18820 | Yellow No. 407 | (EXT. D & C Yellow No. 3) | Acid Yellow 11 |
| C.I.18950 | Yellow No. 402 | | Acid Yellow 40 |
| C.I.19140 | Yellow No. 4 | FD & C Yellow No. 5 | Acid Yellow 23 |
| C.I.20170 | Brown No. 201 | (D & C Brown No. 1) | Acid Orange 24 |
| C.I.20470 | Black No. 401 | (D & C Black No. 1) | Acid Black 1 |
| C.I.42052 | Blue No. 202 | | Acid Blue 5 |
| C.I.42052 | Blue No. 203 | | Acid Blue 5 |
| C.I.42053 | Green No. 3 | FD & C Green No. 3 | Food Green |
| C.I.42085 | Green No. 402 | | Acid Green 3 |
| C.I.42090 | Blue No. 1 | FD & C Blue No. 1 | Food Blue 2 |
| C.I.42090 | Blue No. 205 | D & C Blue No. 4 | Acid Blue 9 |
| C.I.42095 | Green No. 205 | | Acid Green 5 |
| C.I.45100 | Red No. 106 | | Acid Red 52 |
| C.I.45170 | Red No. 213 | (D & C Red No. 19) | Basic Violet 10 |
| C.I.45170 | Red No. 214 | | Solv. Red 49 |
| C.I.45170 | Red No. 215 | (D & C Red No. 37) | Solv. Red 49 |
| C.I.45190 | Red No. 401 | (EXT. D & C Red No. 3) | Acid Violet 9 |
| C.I.45350 | Yellow No. 202-1 | D & C Yellow No. 8 | Acid Yellow 73 |
| C.I.45350 | Yellow No. 202-2 | | Acid Yellow 73 |
| C.I.45370 | Orange No. 201 | D & C Orange No. 5 | Solv. Red 72 |
| C.I.45380 | Red No. 223 | D & C Red No. 21 | Solv. Red 43 |
| C.I.45380 | Red No. 230-1 | D & C Red No. 22 | Acid Red 87 |
| C.I.45380 | Red No. 230-2 | | Acid Red 87 |
| C.I.45410 | Red No. 104-1 | D & C Red No. 28 | Acid Red 92 |
| C.I.45410 | Red No. 218 | D & C Red No. 27 | Solv. Red 48 |
| C.I.45410 | Red No. 231 | | Acid Red 92 |
| C.I.45425 | Orange No. 206 | D & C Orange No. 10 | Solv. Red 73 |
| C.I.45425 | Orange No. 207 | D & C Orange No. 11 | Acid Red 95 |
| C.I.45430 | Red No. 3 | FD & C Red No. 3 | Acid Red 51 |
| C.I.45440 | Red No. 105-1 | | Acid Red 94 |
| C.I.45440 | Red No. 232 | | Acid Red 94 |
| C.I.47000 | Yellow No. 204 | D & C Yellow No. 11 | Solv. Yellow 33 |
| C.I.47005 | Yellow No. 203 | D & C Yellow No. 10 | Acid Yellow 3 |
| C.I.59040 | Green No. 204 | D & C Green No. 8 | Solv. Green 7 |
| C.I.60730 | Violet No. 401 | (EXT. D & C Violet No. 2) | Acid Violet No. 43 |
| C.I.61570 | Green No. 201 | D & C Green No. 5 | Acid Green 25 |
| C.I.73015 | Blue No. 2 | FD & C Blue No. 2 | Acid Blue 74 |

Other representative examples of colorants that are usable in the context of the present embodiments include, natural coloring materials such as, but not limited to, kuchinashi blue, kuchinashi yellow, shisonin, grapeskin extract, cacao pigment, safflower yellow, hibiscus pigment, lac dye, cochineal, shikon, beet red, brazilin curcumin, riboflavin, lutein, carotenoids, annatto), paprika, carminic acid, carmin, anthocyanins, cabbage, chlorophyll, chlorophyllin, copper-chlorophyll, copper-chlorophyllin, caramel and carbomedicinalis.

The light absorbing medium can also be in the form of a film having a thickness in the micrometer or sub-micrometer scale (e.g., thickness of 0.5 μm) and sufficiently high light absorption fraction to elicit the required temperature spikes in the target cells (preferably above 0.2, more preferably above 0.5, more preferably above 0.9 across a wavelength range spanning from IR to UV or a specific band). Representative examples of film materials suitable for the present embodiment include, without limitation, a carbon or graphite film, a film containing metallic nanoparticles such as gold, silver or titanium-oxide, and a film of Bacteriorhodopsin.

Implantation and dispersal of the light absorbing medium can be via any technique known in the art, including, without limitation, local injection of a liquid buffer containing the medium to the target location. For example, in embodiments in which the target location is the retina the light absorbing medium can be injected directly next to or into the retina. In some embodiments of the present invention the medium could also be injected into the vasculature (e.g., directly or via liposomes) for delivery of the medium to the target location via blood flow, etc. Delivery can be based on methods of targeted drug delivery, or it may be supplemented by activation or expression of the medium, e.g., via optical activation. For example, in some embodiments of the present invention, liposomes encapsulated with a dye are introduced into the vasculature, for delivery of the liposome to the target location by the blood stream. Thereafter, the target location is illuminated by light at a wavelength selected to release the dye from the liposomes at the target location. When the light absorbing medium is in the form of a film, it can be implanted at the target location by a minimal invasive or a fully invasive procedure, as known in the art.

At 13 the method directs light to the artificial light absorbing medium, wherein wavelengths and intensities of the light are selected so as to heat the light absorbing medium by light absorption. In various exemplary embodiments of the invention the heating is sufficient to stimulate neurons nearby (e.g., within about 50 μm from) the light absorbing medium. The light is preferably a laser light. For example, the light can be a monochromatic laser light or a combination of several monochromatic laser lights. Lasers which are not strictly monochromatic are also contemplated. In some embodiments of the present invention wavelengths and intensities of the light are selected so as to induce two-photon absorption. This can be done, for example, using ultra-fast light pulses (e.g., femtosecond laser pulses). The use of two-photon absorption is particularly useful in situations in which light scattering can prevent or reduce heating of the neurons at the target location. For example, two-photon absorption can be employed when the target location is at the brain, and it is desired to stimulate neurons beneath the outer surface of the brain. When two-photon absorption is employed the wavelength of the light can be longer than the visible range so as to allow better penetration of the light into buried tissue regions.

Preferably, the intensity and/or wavelength of the light is selected such as to increase the temperature of the light absorbing medium by $\Delta T$, where $\Delta T$ is from about 1° C. to about 10° C., or from about 2° C. to about 7° C., or from about 3° C. to about 6° C., e.g., about 5° C. In various exemplary embodiments of the invention the intensity and/or wavelength of the light is selected such as to generate a substantially abrupt increase of the medium's temperature followed by a sufficiently fast temperature drop. Such temperature change is referred to herein as a "temperature spike".

The rise of temperature within a temperature spike is preferably over a sub-millisecond to several millisecond time scale (e.g., within about 1 milliseconds) but may also be up to 20 milliseconds. The drop of temperature within a temperature spike is preferably over a few milliseconds time scale (e.g., a drop of about 3° C. within about 5 milliseconds), but may also be much longer. A representative example of a temperature spike is provided in FIG. 12 of the Examples section that follows. Under conditions of thermal confinement, a temperature spike reaches the following temperature increase:

$$\Delta T \approx \frac{\alpha \cdot \tau \cdot P}{\pi r^2 d \cdot c_V}$$

Where P (Watt) is the laser power hitting the spot during a pulse of interval $\tau$ (seconds), $\alpha$ is the fraction of incoming power absorbed by the spot of radius r (cm) and along a depth d (cm), and $c_v$=4.2 J/cm$^3$/° C. is the specific heat capacity of water. Thermal confinement occurs approximately when the pulse is shorter than $\tau<\delta^2/\kappa$. where $\delta$(cm) is the characteristic (smallest) dimension and $\kappa=1.3\times10^{-3}$ cm$^2$/sec is the thermal diffusivity of water.

The method ends at 14.

Figure 2:
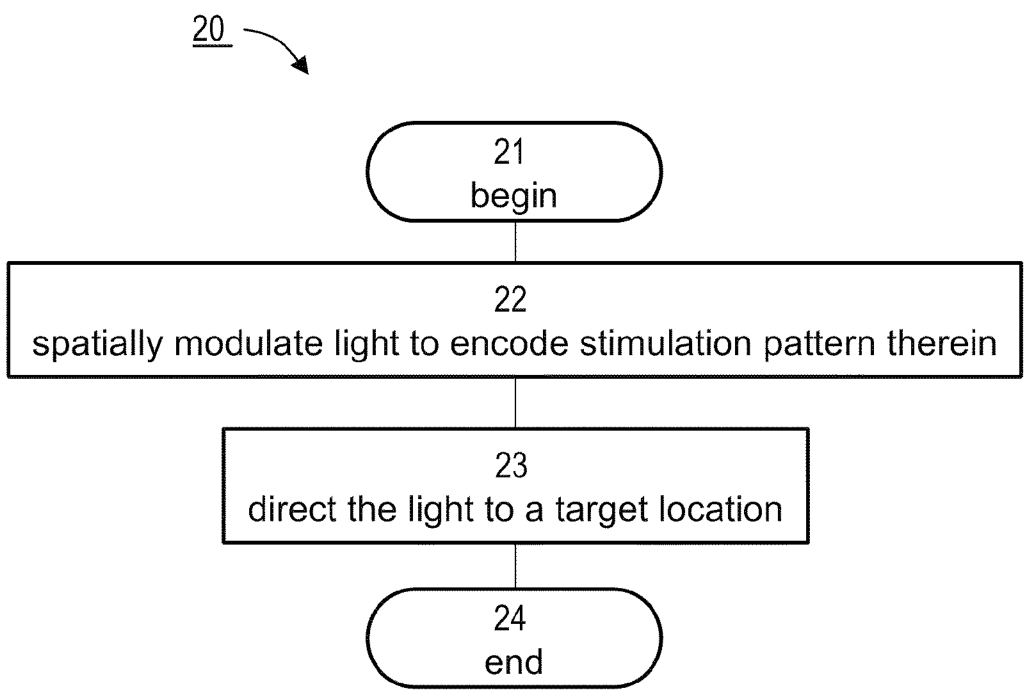

FIG. 2 is a flowchart diagram of another method for stimulating neurons present in a living body, according to various exemplary embodiments of the present invention. The method is referred to hereinunder as method 20.

Method 20 begins at 21 and continues to 22 at which light is spatially modulated to encode a stimulation pattern therein. The light is preferably a laser light. For example, the light can be a monochromatic laser light or a combination of several monochromatic laser lights. Lasers which are not strictly monochromatic are also contemplated.

The stimulation pattern is in accordance with the neurological type of the target location at which the method is executed. For example, when the target location is at the retina or the visual cortex, the stimulation pattern can correspond to visual information, e.g., an image of a scene captured by an imaging device; and when the target location is at the cochlea or the auditory cortex, the stimulation pattern can correspond to acoustic information captured by an acoustical recording device. Other stimulation patterns, e.g., predetermined patterns for treating a neurological condition or disease, or for stimulating a limb to perform an action, are also contemplated.

The stimulation pattern can be two-dimensional or three-dimensional, as desired.

The term two-dimensional stimulation pattern as used herein refers to a pattern engaging a locus at the target location which is substantially a surface. Two-dimensional stimulation pattern may also penetrate, to some extend (e.g., less than 50 μm), to neural tissue beneath the surface. Two-dimensional stimulation pattern can be achieved via single-photon or two-photon absorption mechanisms.

The term three-dimensional stimulation pattern as used herein refers to a pattern engaging a locus at the target location which is substantially a volume. A three-dimensional stimulation pattern penetrates at least 50 μm or at least 100 μm or at least 500 μm or at least 1 mm or at least 2 mm or at least 3 mm beneath the outer surface of the target location. Three-dimensional stimulation pattern can be achieved via two-photon absorption mechanisms.

The spatial modulation of the light can be done by a spatial light modulator, such as, but not limited to, the spatial light modulator disclosed in U.S. Pat. Nos. 5,073,010, 5,130,830, 5,177,628 and 5,844,709, the contents of which are hereby incorporated by reference. A spatial light modulator typically operates according to the principles of light diffraction wherein each elementary unit (e.g., a pixel) of the modulator locally modulates the phase of a portion of a light beam impinging thereon, to provide a predetermined light profile.

A light ray is mathematically described as a one-dimensional mathematical object. As such, a light ray intersects any surface which is not parallel to the light ray at a point. A light beam therefore intersects a surface which is not parallel to the beam at a plurality of points, one point for each light ray of the beam. Generally, a profile of the light beam refers to an optical characteristic (intensity, phase, frequency, brightness, hue, saturation, etc.) or a collection of optical characteristics of the locus of all such intersecting points. Typically, but not obligatorily, the profile of the light beam is measured at a planar surface which is substantially perpendicular to the propagation direction of the light.

The locus of points at which all light rays of the beam has the same phase is referred to as the wavefront of the beam. For collimated light beam, for example, the wavefront is a plane perpendicular to the propagation direction of the light, and the light is said to have a planar wavefront.

Thus, the term "profile" is used to optically characterize the light beam at its intersection with a given surface, while the term "wavefront" is used to geometrically characterize a surface for a given phase.

Since the profile, as explained, can include one or more optical characteristics of a locus of points on a surface, it can be represented by one or more two-dimensional profile functions which return the optical characteristics of a point on the surface, given the two-dimensional coordinates of the point. A general profile function is denoted by $\Gamma_j(\xi,\eta)$, where the index j represents the type of optical characteristic returned by the function (phase, intensity, frequency, etc.) and the tuple $(\xi,\eta)$ represents the coordinates of a point on the surface in an arbitrary coordinate system (Cartesian, polar, parabolic, etc.). Thus, for example, $\Gamma_\phi(x,y)$, $\Gamma_I(x,y)$ and $\Gamma_\nu(x,y)$ returns the phase $\phi$, intensity I and frequency $\nu$ of the light at a point (x,y) in Cartesian coordinate system.

A profile relating to a specific optical characteristic is referred to herein as a specific profile and is termed using the respective characteristic. Thus, the term "intensity profile" refers to the intensity of the locus of all the intersecting points, the term "phase profile" refers to the phase of the locus of all the intersecting points, the term "frequency profile" refers to the frequency of the locus of all the intersecting points, and so on. Similarly to the general profile function, a specific profile function can also be represented by a two-dimensional function.

In various exemplary embodiments of the invention the spatial modulation is a phase-only modulation wherein only the phase varies across the modulator (i.e., non flat phase-profile), but all other optical characteristics are substantially constant across the modulator. In some embodiments the spatial modulation is by means of two modulation-subunits arranged to allow concurrent phase and amplitude modulation of the incoming beam.

The diffraction pattern which modulates the light is also known as a hologram. And the process of forming the diffraction pattern and using it for modulating light is often times referred to in the literature as holography. Thus, the method of the present embodiments generates holographic data which is then reconstructed to provide the desired stimulation pattern. It is appreciated that since the hologram is used for encasing the stimulation pattern, it can be a two-dimensional object, irrespectively of the dimensionality of the stimulation pattern. The advantage of holography is that it allows the generation of high-intensity sparse stimulation patterns with relatively low optical losses.

The method continues to 23 at which the modulated light is directed to the target location so as to form the stimulation pattern thereat. The light is directed by means of optics which may include free-space optics (e.g., an arrangement of lenses, microlens arrays, diffractive elements, etc.) and/or guiding optics (e.g., waveguides, optical fibers, fiber bundles, gradient-index (GRIN) fiber lenses, lens-relay endoscopes, etc.) and/or a generalized phase contrast filter (for transforming phase modulations into intensity modulations). When the target location is the retina of the eye, the optics may optionally include the cornea and lens of the subject. Guiding optics are particularly useful when the target location is not optically accessible by direct illumination.

In some embodiments of the present invention wavelengths and intensities of the light are selected so as to induce two-photon absorption, as further detailed hereinabove.

In various exemplary embodiments of the invention the wavelengths and intensities of the modulated light are selected so as to generate sufficient heat to stimulate neurons by the stimulation pattern. Preferably, the intensity and/or wavelength of the light is selected such the temperature at a spot within the stimulation pattern is increased by $\Delta T$, where $\Delta T$ is from about 1° C. to about 10° C., or from about 2° C. to about 7° C., or from about 3° C. to about 6° C., e.g., about 5° C. In various exemplary embodiments of the invention the intensity and/or wavelength of the light is selected such as to generate a temperature spike, as further detailed hereinabove.

A temperature spike can be achieved, for example, by adjusting the wavelength and/or intensity of the modulated light so as to increase light absorption in specific biological materials present in the target location.

For example, the wavelength and/or intensity and/or spatial distribution of the modulated light can be adjusted such that the light is absorbed by Haemoglobin. Haemoglobin absorbs light from about 380 nm to about 450 nm (absorption peak at about 415 nm) and from about 480 nm to about 600 nm (absorption peak at about 575 nm). Haemoglobin also has a two-photon absorption range of 820-840 nm (absorption peak at about 830 nm).

In some embodiments of the present invention the wavelength and/or intensity of the modulated light are adjusted such that the light is absorbed by Flavoproteins which absorb light from about 400 nm to about 500 nm.

In some embodiments of the present invention the wavelength and/or intensity and/or spatial distribution of the modulated light are adjusted such that the light is absorbed by Lipids (either triglycerides which are mainly present in subcutaneous tissues and around internal organs, or phospholipids which are present in the cells' membrane). Lipids absorb light in the range 880 nm-970 nm.

In some embodiments of the present invention the wavelength and/or intensity of the modulated light are adjusted such that the light is absorbed by Cytochrome c Oxidase. This is the terminal protein in the electron chain within the inner mitochondrial membrane. It has a few absorption peaks in the visible and NIR range (e.g., a peak at about 850 nm).

The method ends at 24.

Figure 3:
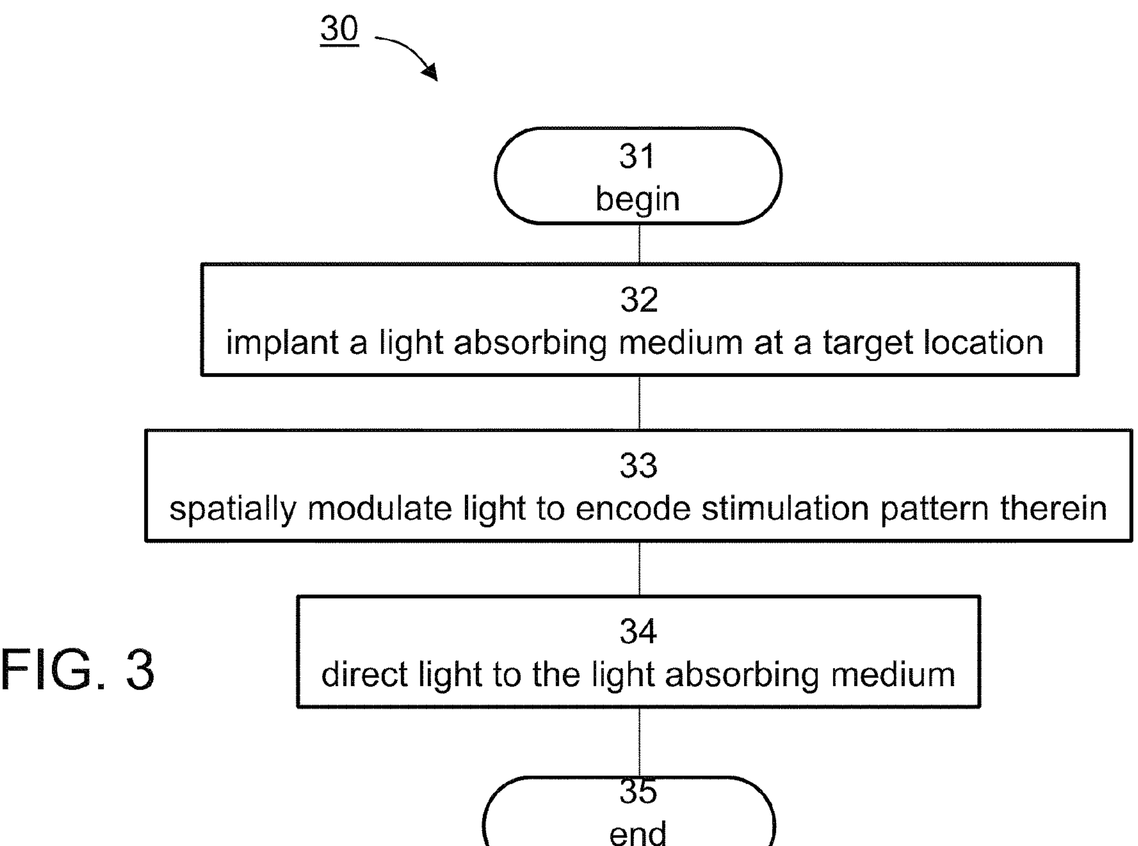

FIG. 3 is a flowchart diagram of another method for stimulating neurons present in a living body, according to various exemplary embodiments of the present invention. The method, referred to hereinunder as method 30, combines several operations of methods 10 and 20.

Method 30 begins at 31 and, optionally and preferably, continues to 32 at which a light absorbing medium is implanted in the target location, as further detailed hereinabove (see, e.g., 12 in FIG. 1 and the accompanying description). Alternatively, the method can be executed after the light absorbing medium has been implanted in the target location. Method 30 can proceed to 33 at which the light is spatially modulated to encode a stimulation pattern therein, as further detailed hereinabove (see, e.g., 22 in FIG. 2 and the accompanying description). The stimulation pattern can be two-dimensional or three-dimensional, as desired.

Method 30 can then proceed to 34 at which the modulated light is directed to the artificial light absorbing medium, wherein wavelengths and intensities of the modulated light are selected so as to heat the light absorbing medium by light absorption, as further detailed hereinabove (see, e.g., 13 in FIG. 1 and the accompanying description, *mutatis mutandis*). In some embodiments of the present invention wavelengths and intensities of the light are selected so as to induce two-photon absorption, as further detailed hereinabove.

The method ends at 35.

Figure 4:
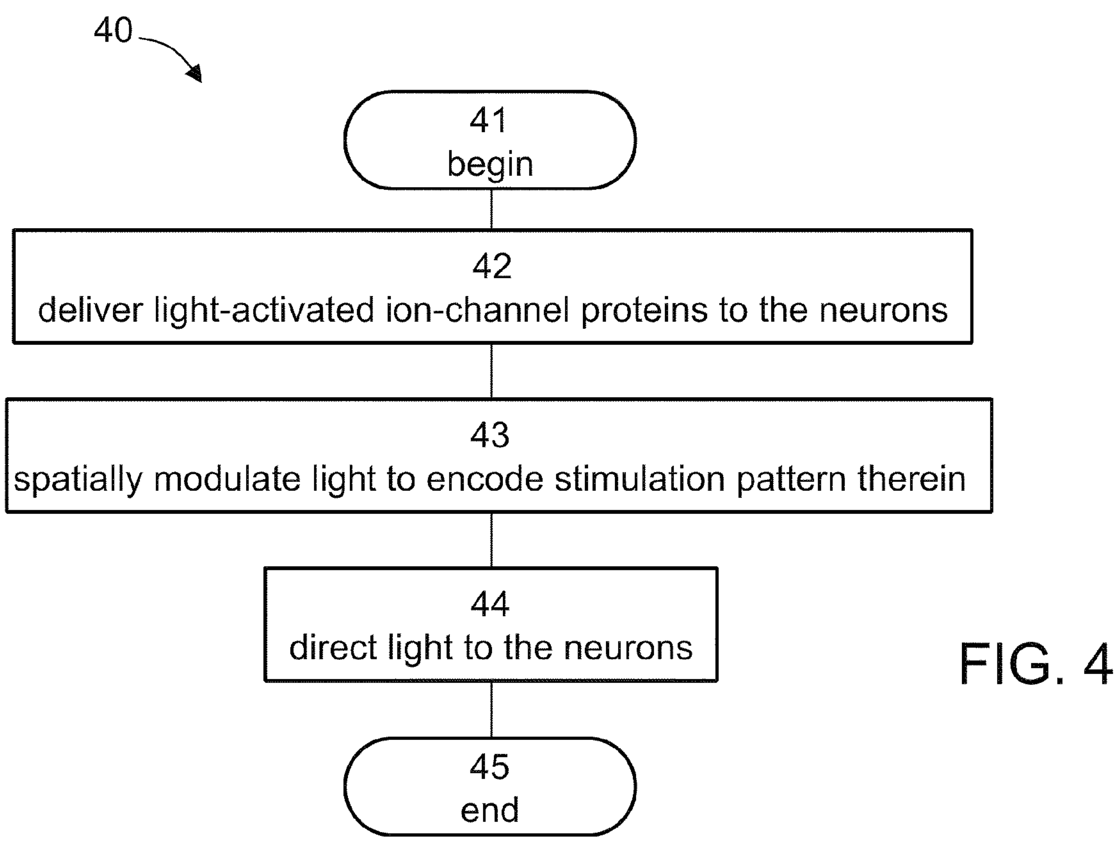

FIG. 4 is a flowchart diagram of another method for stimulating neurons present in a living body, according to various exemplary embodiments of the present invention. The method is referred to hereinunder as method 40.

The method begins at 41 and, optionally and preferably, continues to 42 at which light-activated ion-channel proteins are delivered to the neurons in the target location. Alternatively, the method can be executed after the light-activated ion-channel proteins are delivered to the neurons.

Several types of light-activated ion-channel proteins are contemplated. Representative examples include, without limitation, ChR2, VChR1, NpHR, Chop2, ChR2-310, Chop2-310. In various exemplary embodiments of the invention the light-activated ion-channel protein is ChR2 (ChannelRhodopsin 2) which is a directly light-gated cation-selective ion channel in the green algae Chlamydomonas Reinhardtii. This membrane channel opens rapidly after absorption of a blue photon, generating a large permeability for cations, and can thus be used for depolarizing cells using illumination. Combination of several proteins is also contemplated. For example, in some embodiments of the present invention ChR2, VChR1(Volvox ChannelrhodopsinI) and pHR (Halorhodopsin) are delivered to the target location, wherein ChR2, VChR1 facilitate excitation of neuronal activity and NpHR facilitates inhibiting neuronal activity.

The light-activated ion-channel proteins can be delivered by a technique known in the art. For example, the neurons can be transfected by gene transfer vectors (for example, viruses) capable of inducing expression of photosensitive ion channel (for example, ChR2 ion channels). The vectors can include a nucleic acid sequence that codes for a light-activated ion-channel protein and a cell specific promoter, wherein the targeted neurons express the protein.

For example, viral-based proteins (e.g., lentiviruses or recombinant adeno-associated viruses) can be created to target the neurons, based upon the proteins that they uniquely express. The neurons are then infected by the viral-based gene-transfer proteins, and begin to express a new type of ion channel (for example ChR2), thereby becoming photosensitive.

The method continues to 43 at which light is spatially modulated to encode a stimulation pattern therein, as further detailed hereinabove (see, e.g., 22 in FIG. 2 and the accompanying description). The stimulation pattern can be two-dimensional or three-dimensional, as desired.

In various exemplary embodiments of the invention the wavelengths and/or intensities of the shapes forming the stimulation pattern are selected so as to activate the light-activated ion-channel proteins. For example, blue light spots can be used to activate ChR2 and green-yellow light spots can be used to activate VChR1 and NpHR.

The method continues to 44 at which the modulated light is directed to the target location so as to form the stimulation pattern thereat. The wavelengths and intensities of the light are selected so as to activate the light-activated ion-channel proteins. In some embodiments of the present invention wavelengths and intensities of the light are selected such that the light-activated ion-channel proteins are activated by two-photon absorption. This can be done, for example, using ultra-fast light pulses, as further detailed hereinabove.

The light is directed by means of optics which may include free-space optics (e.g., an arrangement of lenses, microlens arrays, diffractive elements, etc.) and/or guiding optics (e.g., waveguides, optical fibers, fiber bundles, gradient-index (GRIN) fiber lenses, lens-relay endoscopes, etc.) and/or a generalized phase contrast filter (for transforming phase modulations into intensity modulations). When the target location is the retina of the eye, the optics may optionally include the cornea and lens of the subject. Guiding optics are particularly useful when the target location is not optically accessible by direct illumination.

The method ends at 45.

Reference is now made to FIGS. 5A-E which are schematic illustrations of a neurostimulation system 50, according to various exemplary embodiments of the present invention.

Figure 5A:
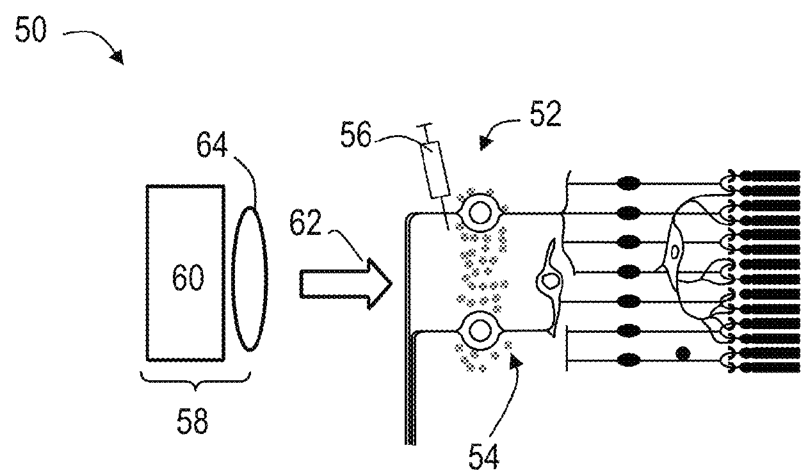
Figure 5A:
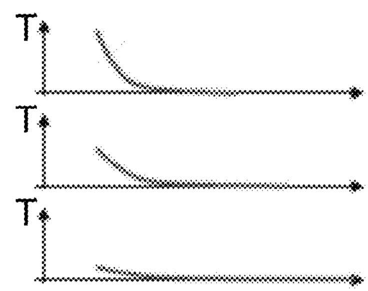
Figure 5B:
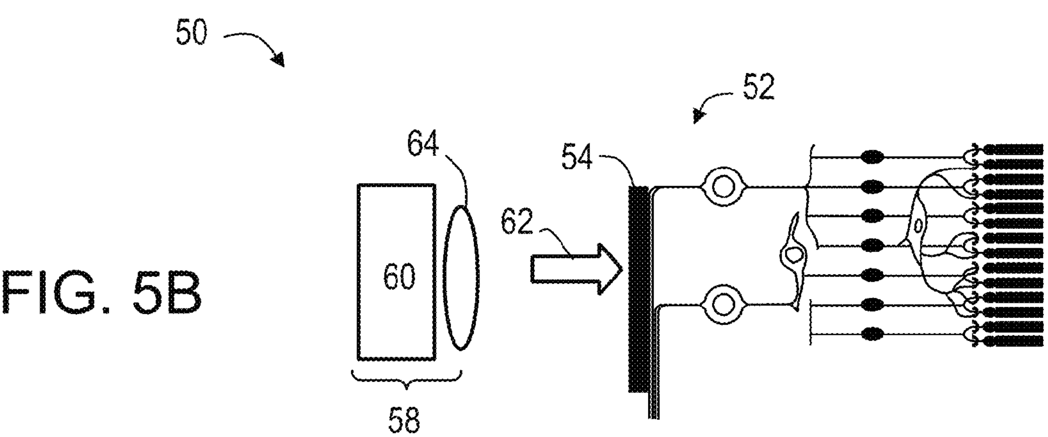
Figure 5B:
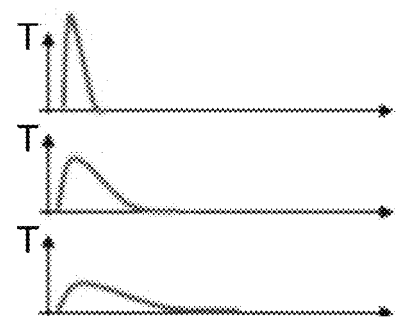
Figure 5C:
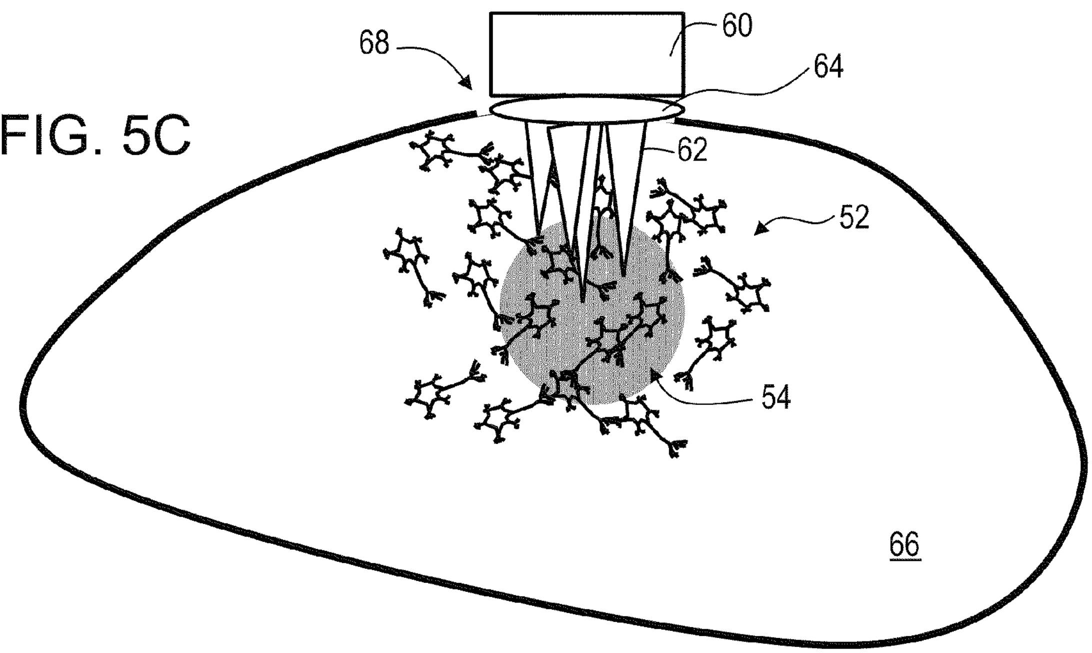
Figure 5D:
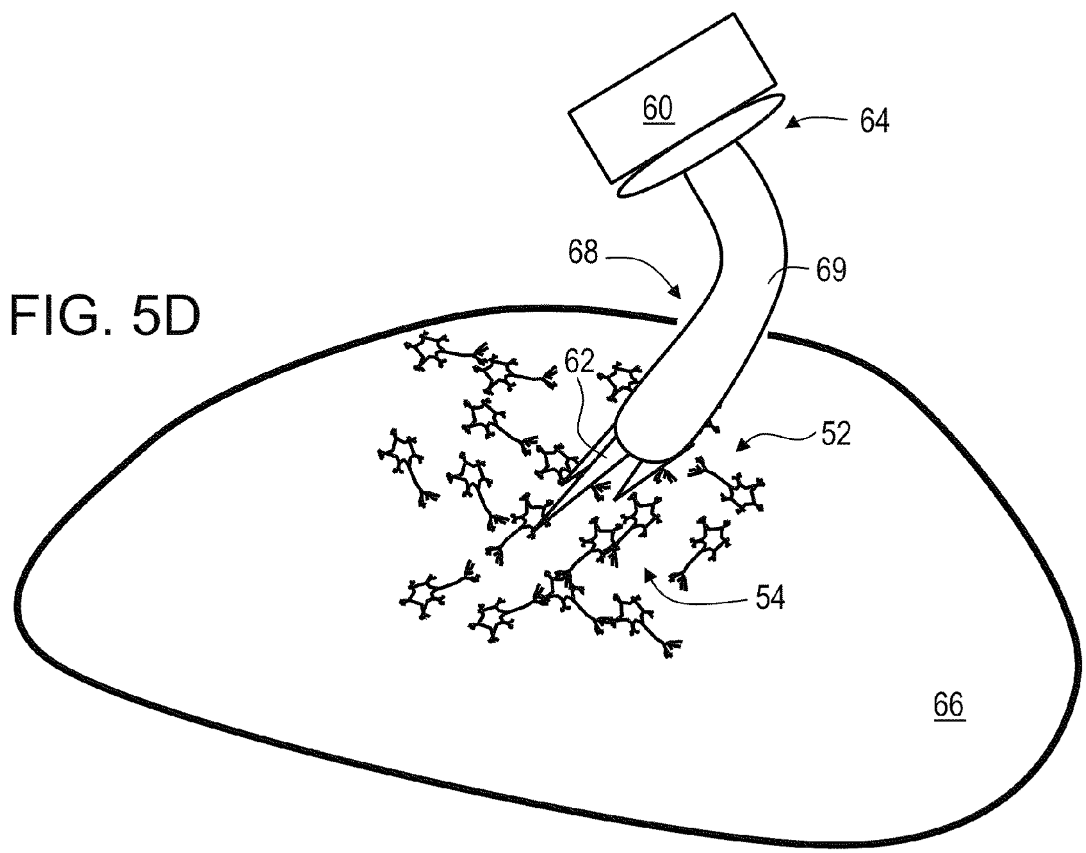
Figure 5E:
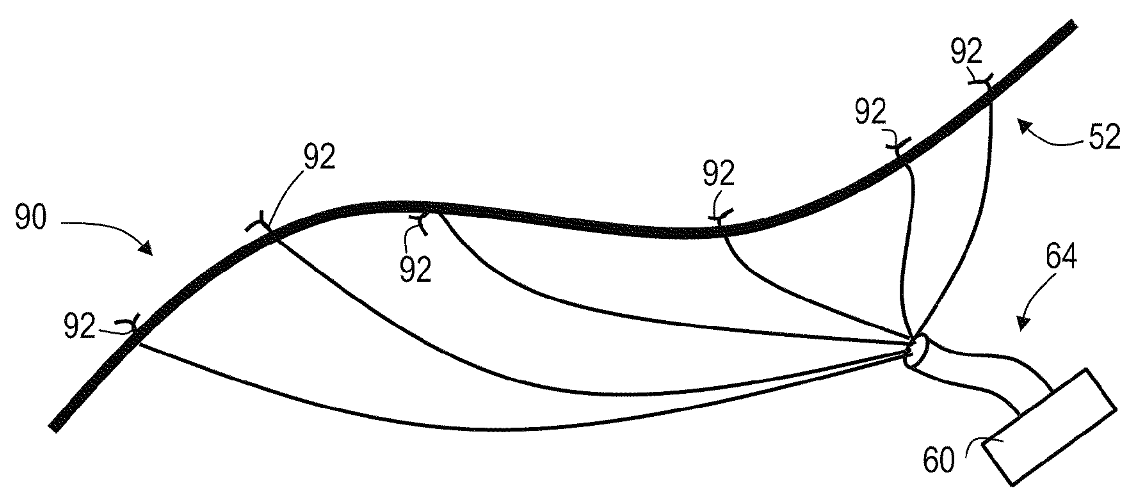

System 50 can be used for stimulating neurons at a target location 52, such as, but not limited to, a retina, a cochlea, a cortex, a brainstem structure, a spinal cord or any location in the living body in which there is a large population of neural tissues, as further detailed hereinabove. The target location shown in FIGS. 5A-B is a retina, the target location shown in FIGS. 5C-D is the cerebral cortex, and the target location shown in FIG. 5E is the cochlea, but it is to be understood that more detailed reference to a retina, cerebral cortex or cochlea is not to be interpreted as limiting the scope of the invention in any way.

In some embodiments of the present invention, target location 52 is implanted with an artificial light absorbing medium 54. Medium 54 can be in the form of a plurality of particles, as illustrated in FIGS. 5A, 5B and 5C or in the form of a film as illustrated in FIG. 5B. Any of the aforementioned types of light absorbing media can be implanted in target location 52. In various exemplary embodiments of the invention medium 54 is implanted extracellularly in target location 52. The syringe 56 illustrated in FIG. 5A represents an embodiment in which medium 54 is implanted in target location 52 by means of local injection. However, this need not necessarily be the case, since, for some applications, it may be desired to employ other implantation techniques as further detailed hereinabove. For clarity of presentation, medium 54 is not shown in FIG. 5E, but one of ordinary skill in the art would appreciate that medium 54 may be delivered to the cochlea, if desired, by any of the aforementioned techniques.

System 50 comprises an illumination system 58 having a light source 60 for generating light 62 and optics 64 for directing light 62 to target location 52. When target location 52 is implanted with artificial light absorbing medium 54, wavelengths and/or intensities and/or spatial distribution of light 62 are selected so as to heat medium 54 by light absorption, hence to stimulate neurons nearby medium 54, as further detailed hereinabove. When target location 52 is not implanted with artificial light absorbing medium, wavelengths and/or intensities and/or spatial distribution of light 62 are selected so as to so as to increase light absorption in specific biological materials present in the target location, hence to heat the neurons and stimulate them, as further detailed hereinabove. When the neurons at target location 52 are transfected by gene transfer vectors capable of inducing expression of photosensitive ion channel, wavelengths and/or intensities and/or spatial distribution of light 62 are selected so as to activate the light-activated ion-channel proteins.

Light source 60 is preferably a laser light. For example, light source 60 can be a monochromatic laser light or a combination of several monochromatic laser lights. Lasers which are not strictly monochromatic are also contemplated. When several lasers are employed, they can operate in synchronization (simultaneously or in a time-multiplexed manner).

The graphs shown in FIGS. 5A-B show the temperature profile of medium 54 at three different time instants, immediately following the illumination (top graph of each Figure), about 1 ms following the illumination (middle graph of each Figure) and about 5 ms following the illumination (middle graph of each Figure). As shown, in the embodiment shown in FIG. 5B, the peak temperature is higher compared to the embodiment shown in FIG. 5A to insure that the temperature spike experienced by the cells will be sufficiently high to excite them.

In various exemplary embodiments of the invention illumination system 58 comprises a projector system which generates a spatially modulated light beam encoded with a stimulation pattern, as further detailed hereinabove. A more detailed description of a projector system is provided hereinunder. The stimulation pattern formed at the target location by the projector system can be two-dimensional or three-dimensional. When the projector system provides a two-dimensional stimulation pattern, it can be configured to induce a single-photon or a two-photon absorption. When the projector system provides a three-dimensional stimulation pattern, it is preferably configured to induce a two-photon absorption, as further detailed hereinabove.

Optics 64 can be a free-space optics and/or guiding optics, as further detailed hereinabove.

With specific reference to FIG. 5C, free-space or guiding optics 64 can focuses light 62 through a hole 68 burred in the skull directly unto target location 52 at cerebral cortex 66. Optical stimulation of neurons buried up to about 300 μm from the surface of the cerebral cortex 66 can be achieved according to various exemplary embodiments of the present invention via linear single-photon or non-linear two-photon optical effects. Optical stimulation of neurons buried up to 2 mm from the surface of the cerebral cortex, can be achieved according to various exemplary embodiments of the present invention using ultrafast lasers pulses to generate nonlinear two-photon optical effects.

With specific reference to FIG. 5D optical stimulation of neurons buried at any distance, can be achieved according to various exemplary embodiments of the present invention by focusing a laser outside the skull unto the entrance aperture of an optical fiber or fiber bundle 69 to achieve single-point controlled excitation. Alternatively, a holographic pattern as described above can be reconstructed unto the entrance aperture of an image-preserving endoscopic device which guides the light through the skull and brain and then re-image the patterns onto target location 52. Devices with appropriate dimensions (mm or sub-mm) are typically prepared as bundles of fibers, gradient-index (GRIN) fibers or relay-lens boroscopes. Bundles of fibers have the advantage of flexibility. The endoscopic device can have a lens at the implanted end (typically a GRIN lens). The endoscopic device may also be terminated with a side-firing prism or minor surface e.g., for reducing tissue damage.

With specific reference to FIG. 5E, when the target location is the cochlea 90, light source 60 can be placed distal to the cochlea 90 in operation, for instance, under the scalp or within a behind-the-ear housing for a speech processor. Alternatively, the light source can be in a box positioned, for example, on the hip. Guiding optics 64 can focus the light (not shown) to a plurality of auditory neurons 92 in cochlea 90, e.g., by means of a plurality of optical fibers that are implanted in cochlea 90 and are optically coupled to light source 60. Alternatively, side-emitting waveguides can be utilized as optics 64.

Reference is now made to FIG. 6 which is a schematic illustration a neurostimulation device 70, according to various exemplary embodiments of the present invention. Device 70 forms a stimulation pattern at target location 52 and can be used for stimulating neurons present at the target location whether or not the target location is implanted with artificial light absorbing medium 54. Device 70 can also be used for stimulating neurons when the neurons express light-activated ion-channel proteins.

Device 70 comprises a projector system 72 which generates a spatially modulated light beam encoded with a stimulation pattern. Projector system 72 can comprise one or more light sources 74 which generate read light 82, and a spatial light modulator (SLM) 76 which performs the modulation.

Although device 70 is shown as having two light sources, this need not necessarily be the case, since device 70 can have any number of light sources, depending, for example, on the number of different specific wavelength bands which are required to stimulate the neurons.

Generally, SLM 76 comprises an address unit 78 and a modulation unit 80. Address unit 78 receives a pattern from an external source 88 and alters optical characteristic of modulation unit 80. The spatial variations of optical characteristic across modulation unit 80 are known as a hologram. Modulation unit 80 receives and modulates read light 82 in accordance with the hologram. Thus, SLM 76 modulates read light 82 in accordance with the pattern signal to provide modulated light 84 constituting a reconstructed stimulation pattern.

Address unit 78 can be either electrically-addressable in which case it receives an electric pattern signal, or optically-addressable, in which case it receives an optical pattern signal, also known as "write light" (not shown). External source 88 can include a data processor which calculates the pattern and transmits it to unit 78 either as electrical signals or as optical signals.

Modulation unit 80 can comprise a nematic liquid crystal, or a ferroelectric liquid crystal (FLC), the latter being preferred from the standpoint of high response speed. Modulation unit 80 can also comprise an array of mirrors or micro-mirrors capable of moving over a full wavelength allowing 2π of phase control. Other MEMS based modulation units and spatial light modulators are not excluded from the scope of the present invention.

In various exemplary embodiments of the invention modulation unit 80 provides a modulated light beam 84 having a substantially flat intensity profile but non-flat phase profile, as further detailed hereinabove. In various exemplary embodiments of the invention modulation unit 80 induces a phase-only modulation, as further detailed hereinabove. In some embodiments, the modulation unit comprises two modulation-subunits arranged to allow concurrent phase and amplitude modulation of the incoming beam.

Spatial light modulators suitable for the present embodiments are disclosed in U.S. Pat. Nos. 5,073,010, 5,130,830, 5,177,628 and 5,844,709, the contents of which are hereby incorporated by reference.

Read light 82 from the light source(s) can be directed to modulation unit 80 of SLM 76 via one or more optical redirecting and focusing elements. In the representative example illustrated in FIG. 6, the light beam from a first source 74*a* is redirected by a minor M and passes through a dichroic minor DM which is selected to allow transmission of the light from first source 74*a* but reflect light from a second source 74*b*. Light beam from second source 74*b* is therefore combined with the beam from source 74*a* at diachronic mirror DM to form read light 82. The two beams are expanded using a beam expander BE to impinge on a polarizing beam splitter BS which redirects the read light to modulation unit 80. The stimulation pattern is encoded in the read light by modulation unit 80 which provides a modulated light 84. Light 84 is projected out of projector system 72 via beam splitter BS. It is to be understood, that read light 82 can be directed to SLM 76 in various other ways, all of which are known to those skilled in the art of optics.

The stimulation pattern formed at the target location by projector system 72 can be two-dimensional or three-dimensional, as further detailed hereinabove.

Device 70 can also comprise optics 86 which directs the modulated light 84 to target location 52. Optics 86 can be free-space optics (e.g., an arrangement of lenses, microlens arrays, diffractive elements, etc.) and/or guiding optics (e.g., waveguides, optical fibers, fiber bundles, gradient-index (GRIN) fiber lenses, lens-relay endoscopes, etc.) and/or a generalized phase contrast filter (for transforming phase modulations into intensity modulations). When the target location is the retina of the eye, the optics may optionally include the cornea and lens of the subject. Guiding optics are particularly useful when the target location is not optically accessible by direct illumination. In the representative embodiment illustration of FIG. 6, free-space optics is shown. In this embodiment, optics 86 includes a telescope which is optically coupled to microscope objective. The telescope and microscope are arranged to form the reconstructed pattern on the objective L3 of the microscope.

Reference is now made to FIG. 7 which is a schematic illustration of a neuroprosthesis system 100, according to various exemplary embodiments of the present invention. System 100 comprises a neurostimulation device 102 and a sensing device 104. In various exemplary embodiments of the invention the principles and operations of neurostimulation device 102 are similar to the principles and operations of device 70. In some embodiments of the present invention are similar to neurostimulation device 102 is device 70.

Sensing device 104 serves for sensing information from the environment 106 and transmitting signals 108 pertaining to the sensed information to neurostimulation device 102. Device 102 calculates a stimulation pattern (e.g., by means of a data processor as further detailed hereinabove) based on the information and directs a modulated light 84 encoding the stimulation pattern to target location 52.

Sensing device 104 can be embodied in many forms. In some embodiments of the present invention sensing device 104 collects visual information. For example, sensing device 104 can be an imaging device which captures an image of a scene and transmits it to neurostimulation device 102. In these embodiments, the stimulation pattern corresponds to visual information and the target location is the retina or the visual cortex. In some embodiments of the present invention sensing device 104 collects acoustical information. For example, sensing device 104 can include a microphone which collects acoustic waves from the environment and converts them to electrical signals and a transmitter which transmits the signals to neurostimulation device 102. In these embodiments, the stimulation pattern corresponds to the acoustic information and the target location is the cochlea or the auditory cortex. Other types of sensing devices are not excluded from the scope of the present invention.

System 100 or part thereof can be mounted on the subject by any known technique. For example, when system 100 is used to stimulate neurons in the retina, sensing device 104 and optionally also projector system 72 can be mounted on a head-up display as known in the art. Alternatively, sensing device 104 and/or projector system 72 can be miniaturized and implanted in the eye. When system 100 is used to stimulate neurons in the cochlea, sensing device 104 can be miniaturized and mounted in or behind the ear and projector system 72 is miniaturized and implanted in the cochlea.

It is expected that during the life of a patent maturing from this application many relevant light modulators will be developed and the scope of the term spatial light modulator is intended to include all such new technologies a priori.

Attention will now be given to the advantages and potential applications offered by some embodiments of the present invention.

Embodiments of the present invention can be used to drive complex neural activity patterns containing many action potentials (of the order of millions) per second.

By controlling or perturbing neuronal dynamics, the present embodiments can be used in academic neuroscience research as well as in many medical applications, e.g., the treatment of a neurological condition.

Some embodiments of the present invention can be used for the treatment of blindness. Some of the most common causes of blindness are degenerative diseases of the outer retina, like Age-related Macular Degeneration (AMD) and Retinitis Pigmentosa (RP), globally affecting approximately 25-30 million and 1.5 million individuals respectively. Diseases of the outer retina result in photoreceptor loss, while the inner retinal neurons and in particular the retinal ganglion cells and their optic nerve projections are largely maintained functional. The present embodiments can be used for artificially stimulating these relatively well-preserved nerve cells hence to provide at least partial vision restoration for the blind. In some embodiments, vision restoration or partial vision restoration is achieved by stimulating neurons in other locations along the visual pathway (e.g., the optic nerve, the Lateral Geniculate Nucleus or primary visual cortex).

Some embodiments of the present invention can be used for stimulating the auditory system of the living subject. For example, in some embodiments of the present invention a cochlear implant is provided, wherein light is used for stimulating auditory neurons to evoke action potentials therein. The cochlear implant can be implanted into the scala tympani of the cochlea, or in an alternate downstream location along the auditory pathway, to provide sound perception for deaf individuals.

Some embodiments of the present invention can be used for Deep-Brain Stimulators (DBS) or Vagal Nerve Stimulators (VNS) for the treatment of many types of neurological as well as psychiatric conditions, e.g., without limitation dystonia, epilepsy, tourette's syndrome, vegetative state, metabolic disorder (e.g., obesity), mood disorders (e.g., depression and bipolar disorder), anxiety disorders (e.g., generalized anxiety disorder and obsessive-compulsive disorder), chronic pain (e.g., visceral pain, neuropathic pain, nociceptive pain, phantom-limb pain), gastrointestinal disorders (e.g., gastroesophageal reflux disease (GERD), fecal dysfunction, gastrointestinal ulcer, gastroparesis, and other gastrointestinal motility disorders), hypertension, cardiac disorders (e.g., tachycardia, bradycardia, other arrhythmias, congestive heart failure, and angina pectoris), psychotic disorders (e.g., schizophrenia), cognitive disorders, dementia (e.g., Alzheimer's disease, Pick's disease, and multi-infarct dementia), eating disorders (e.g., anorexia nervosa and bulimia), sleep disorders (e.g., insomnia, hypersomnia, narcolepsy, and sleep apnea), endocrine disorders (e.g., diabetes), movement disorders (e.g., Parkinson's disease and essential tremor), and/or headache (e.g., migraine and chronic daily headache).

DBS and VNS stimulations can be executed either for treating a particular occurrence of a syndrome, or for treating a chronic condition. For treatments of chronic conditions by DBS, some embodiments of the present invention provide an implantable chronic stimulation device which is adapted for intra-skull implantation.

For treatments of chronic conditions by VNS, some embodiments of the present invention provide an implantable stimulation device which is adapted for implantation adjacent to the vagus nerve.

Some embodiments of the present invention can be used as a laboratory equipment, e.g., for stimulating neurons in an ex-vivo neuron culture.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Some embodiments of the present invention allow controlling neuronal circuits with cellular resolution. This is useful in many medical applications because neighboring neurons in real circuits are often found to have widely divergent response properties.

The present embodiments are advantageous over optical excitation of traditional optogenetic populations, since traditional techniques are limited to nonspecific population-wide flashes of light delivered using planar whole-field illumination or delivered to deep brain structures using implanted optical fibers [see, e.g., Aravanis, A. M. et al. "An optical neural interface: in vivo control of rodent motor cortex with integrated fiberoptic and optogenetic technology," J Neural Eng 4, S143-56 (2007)]. Some techniques allow patterned neural photo-excitation via a modality known as neurotransmitter uncaging [see, e.g., Shoham, S., O'Connor, D. H., Sarkisov, D. V. & Wang, S. S.-H. "Rapid neurotransmitter uncaging in spatially defined patterns," Nature Methods 2, 837-843 (2005)]. These techniques, however, employ rapid random-access laser deflection, which has a very limited ability to flexibly stimulate large populations because of the relatively long, millisecond-scale, dwell time each neuron requires. More recently, parallel photo-stimulation systems using microdisplays based on micro-mirror arrays have been developed [Reutsky, I., Ben-Shimol, D., Farah, N., Levenberg, S. & Shoham, S. in CNE '07. 3rd International IEEE/EMBS Conference on Neural Engineering, 2007 50-52 (2007); Wang, S. et al. "All optical interface for parallel, remote, and spatiotemporal control of neuronal activiy," Nano Lett 7, 3859-63 (2007)]. However, these systems require very strong light sources due to their spectacular inefficiency when used for projecting a typical sparse, intense excitation pattern.

The need for an optical tool which can be optimized for optogenetic photo-stimulation of large neuron populations has led the present inventor to devise a technique for stimulating neurons by spatial light modulation. The technique of the present embodiments combines parallel simultaneous photo-stimulation of multiple locations in two or three dimensions with high intensity and efficiency that are characteristic of sequential deflection methods.

It is noted that spatial light modulation has heretofore been employed in the field of multi-focal optical tweezers [Dufresne, E. R., Spalding, G. C., Dearing, M. T., Sheets, S. A. & Grier, D. G. Computer-generated holographic optical tweezer arrays. Review of Scientific Instruments 72, 1810-1816 (2001)].

The present Example describes experiments performed according to the teachings of the present embodiments.

The experimental setup and the procedure are schematically illustrated in FIGS. 8A-C. Polarized laser light from two sources is combined using a dichroic minor and expanded. The expanded beam is modulated by a spatial light modulator which constitutes a hologram thereon, and imaged through a telescope to form a reconstruction pattern at the back aperture of a microscope objective. The reconstruction patterns in the Fourier plane serve to excite or inhibit nerve cells expressing light-gated ion channels in their cell membranes. FIG. 8B is a magnification of a portion of the nerve cells sample (see box 200 in FIG. 8A), and FIG. 8C illustrates the process of stimulation of a single neuron (see, e.g., circle 202 in FIG. 8B). The experiments are described in more details in the Methods section below.

In Fresnel holography, field patterns on a spatial light modulator are related to the resulting stimulation pattern through the Fresnel transform:

$$E_{stim}(\bar{\rho}, z) = \int_z E_{SLM}(\bar{r}) e^{-2\pi i \frac{\bar{r}\cdot\bar{\rho}}{\lambda f}} e^{2\pi i \frac{z\rho^2}{\lambda f^2}} d\rho = \mathcal{F}\left[E_{SLM}(\bar{r}) e^{2\pi i \frac{z\rho^2}{\lambda f^2}}\right],$$

where $\bar{r}=(x, y), \bar{\rho}=(u, v)$ are the SLM and the stimulation coordinates respectively, z is the distance from the focal plane and $\Im$ is a scaled Fourier transform. To generate a set of M stimulation points with the 3-D coordinates $\{u_m, v_m, z_m\}$ and intensity $\epsilon_m^2$, the required field is:

$$E'_{SLM} = \sum_{m=1}^{M} \varepsilon_m e^{2\pi i \frac{\bar{\rho}_m \cdot \bar{r}}{\lambda f}} e^{-2\pi i \frac{z_m r^2}{\lambda f^2}}.$$

$E'_{SLM}$ contains both amplitude and phase information. According to various exemplary embodiments of the present invention $E'_{SLM}$ is approximated using a phase-only modulation of an input laser beam in a discrete pixel matrix. Phase-only modulation allows the entire incoming beam power to be diffractively distributed between the stimulation points with minimal power loss. In practice, the efficiency is limited by technical design parameters, such as the SLM reflectivity and the like, and by the inherent approximability of arbitrary stimulation patterns by phase-only SLM images (about 85% with continuous phase modulation and about 30% with binary phase modulation). In the present example, binary phase modulation was employed.

FIG. 8D shows a phase image used to generate a typical sparse pseudo-random pattern of photo-stimulation points. For pseudo-random stimulation patterns the SLM phase image can be computed rapidly using a single-step Fourier transform. For inherently symmetric stimulation grids, on the other hand, computation of the phase modulation image typically requires more cycles of iterative algorithms, and may have lower overall diffraction efficiency. It was found by the present inventors that highly symmetric stimulation patterns can be achieved by pseudo-random division of stimulation points between several frames and displaying these frames in an alternating matter. Such procedure creates enough randomness for efficient holograms.

The spatial range of photo-stimulation loci is primarily limited by the inherent spatial sampling performed by the SLM's pixel matrix (with pitch Δ). Comparison of the required bandwidth for a single stimulation point (see Equation for $E'_{SLM}$ above) to the SLM's bandwidth limitation of 1/(2Δ) in each axis, defines a rectangular dipyramid of accessible locations:

$$B(E)_{x,y} = \begin{cases} \frac{|u|}{\lambda f} + \frac{|z|}{\lambda f^2} L \le \frac{1}{2\Delta} \\ \frac{|v|}{\lambda f} + \frac{|z|}{\lambda f^2} L \le \frac{1}{2\Delta}, \end{cases}$$

where L is the SLM length. Outside the locus, L can be effectively decrease to reduce the $2^{nd}$ term $$\left(L^{eff} = \frac{\lambda f^2}{2\Delta \cdot z_m} - \frac{u_m f}{z_m}\right)$$

by truncating phase patterns, at the price of bigger, less efficient spots.

FIG. 9A shows the theoretical spatial distribution of efficiency within the "accessible" dipyramid:

$$\eta \propto \frac{L_x^{eff} L_y^{eff}}{L^2} \int_{-\frac{\Delta v}{2}}^{\frac{\Delta u}{2}} \int_{-\frac{\Delta v}{2}}^{\frac{\Delta v}{2}} F(E_{SLM}) \cdot \mathrm{sinc}(v\Delta v) \cdot \mathrm{sinc}(u\Delta u) \cdot du\, dv$$

$$\text{where } \Delta u = \frac{\lambda f}{N\Delta x}, \Delta v = \frac{\lambda f}{N\Delta y},$$

and the sinc functions result from the effective filtering performed by square SLM pixels. This theoretical prediction is well matched with experimental measurements of the spatial efficiency distribution along the x and z-axes (FIGS. 9B-C). To remove the effect of these efficiency inhomogeneities in the x-y plane, $\epsilon_m$ was set to be inversely proportional to a spatial sinc function (FIG. 9D). The intensity of each individual stimulation spot can be individually controlled by varying the intensity $\epsilon_m^2$ in the equation for $E'_{SLM}$. This method of control provides excellent linearity and at least 256 gray levels (FIG. 9E).

The average power density at each stimulation point is inversely proportional to the number of points simultaneously addressed. In this embodiment, an intensity of 10 mW/mm$^2$ is approximately required to activate the neurons. This limits the total number of simultaneously accessible points to ~250 when the guiding optics is a ×4 microscope objective, or more then 1000 when the guiding optics is a ×10 microscope objective (FIG. 9F).

A typical diameter of a nerve cell is approximately 10 μm, and the optogenetic channels to be illuminated are distributed in a roughly spherical geometry on the cell's outer membrane. Unlike in typical imaging and optical tweezer scenarios, the size and Gaussian spatial distribution of diffraction limited spots is non-optimal:

$$W_O(z) = \alpha \frac{\lambda(f+z)}{L^{eff}}$$

In accordance with preferred embodiments of the present invention the spot size was modified by adjusting the objective effective numerical aperture, NA.

The axial resolution is determined by objective's numerical aperture. Note that there are small changes in the numerical aperture for different Z.

$$\Delta z \propto \frac{\lambda}{NA'^2} = \frac{\lambda}{n^2 \sin^2\left(\arctan\left(\frac{L}{2(f+z)}\right)\right)}$$

The temporal resolution of the system according to various exemplary embodiments of the present invention is determined by the SLM refresh rate. A typical figure of rise and fall time for a ferroelectric-based SLM, is about 50 μs. The typical time-scale for neural stimulation is of the order of 1 millisecond. This difference in time-scale can be used for time-multiplexing of several lasers with different wavelengths, thus enabling the activation of different ion channels.

Since diffraction efficiency is less than unity, some of the stimulation power is directed to unwanted areas in the stimulation volume, resulting in noise. For low-symmetry patterns, this noise is distributed fairly uniformly.

In some embodiment of the present invention, the guiding optics generates a stimulation spot of Gaussian shape with a full width at half maximum diameter of 5 mm with a ×10 objective (FIG. 10A). The size of the spot affects the system performance. The spot size can be controlled by changing various parameters of the system. For example, by modifying the diameter of the laser beam illuminating the SLM, the spot size can be changed significantly (FIG. 10B, lower marks for ×10objective, upper marks for ×4 objective). The spot size can also be modified by axially shifting the entire stimulation pattern, thus modifying the objective numerical aperture (FIG. 10C). Large contiguous spots with possibly arbitrary shapes can be generated by tiling individual spots adjacent to each other. In phase-only holography, this results in speckle noise that may disrupt the uniformity of the spot (FIG. 10D, left image and its corresponding section). By time averaging over shifted versions of the holograms, speckle can be eliminated and a uniform spot can be achieved (FIG. 10D, right image and its corresponding section).

The response time of our system, based on a fast ferroelectric liquid crystal, is sub-millisecond. This enables stimulation pulses as short as 0.5 ms (FIG. 10E). This response time may also be utilized for time sharing of several different wavelengths, each stimulating a different population of neurons. An example is a dual-wavelength image with 1 msec refresh rate (FIG. 10F).

Methods

Stimulation

The optical setup consisted of two DPSS lasers, a green laser (532 nm, 200 mW) and a blue laser (473 nm, 50 mW) (Viasho Lasers, China). Beam expansion was performed by a 1:4 Galilean telescope. The diameter of the expanded beam was approximately 4 mm (FWHM). The expanded beam was reflected by a polarizing beam splitter onto the SLM. The SLM was a ferroelectric liquid-crystal micro-display (SXGA-R3, Forth Dimension Displays, UK) with a 30° switching angle and a 13.6 μm pixel pitch.

The incoming polarized light incident on each pixel was rotated with either a positive or negative switching angle, depending on the pixel's state. The polarizing beam splitter passes only the perpendicular component of the outgoing light, effectively creating a phase-only binary hologram with [0,π] modulation. Only the central 512×512 pixels of the SLM were used for displaying the hologram, so as to speed up calculations, at the expense of a larger spot size.

The modulated wavefront was imaged by a Keplerian 2:1 telescope to the back aperture of a microscope objective, to avoid vignetting. The telescope de-magnification increased the maximal diffraction angle. The objective was part of an inverted microscope (TE-2000U, Nikon, Japan), and the second lens of the telescope served also as the microscope's tube-lens. The first lens of the telescope created an intermediate image outside the microscope, where unwanted diffraction orders were blocked by the placement of a rectangular slit. Different microscope objectives may be used to obtain different combinations of resolution, field and spot size. Both a ×10 (NA=0.25, 20 mm focal length) and an ×4 (NA=0.13, 50 mm focal length) were used to obtain a 0.6×0.7 mm or a 1.5×1.75 mm field, respectively.

A CCD camera (Hammamatsu, Japan) was attached to the microscope, and used to record the resulting stimulation patterns, as well as fluorescence and bright-field images of the neural specimens. This was also used to align the stimulation pattern with the specimen.

The binary holograms were calculated by the "Randomal Superposition" method as described in DiLeonardo et al. "Computer generation of optimal holograms for optical trap arrays," Opt. Express 15, 1913-1922 (2007). The target stimulation pattern was multiplied by a random phase mask, and was then transformed by inverse Fourier transform. The binary phase was obtained from the inverse transform by the following binarization transformation:

$$E'_{SLM}(x_i,y_j)=\mathrm{sgn}[Re(E_{SLM}(x_i,y_j))],$$

where $x_i,y_j$ are the coordinates of the center of the pixel.

A single 512×512 hologram was calculated in 44 ms by an Intel Core2 Q9300 2.5 GHz personal computer. Numerical processing was done by MATLAB software (mathworks, USA).

For highly symmetric patterns, a GSW algorithm (see DiLeonardo et al. supra) was used. The hologram sequence was transferred to the SLM through a DVI interface. Precise control over video timing was achieved by using the Psychtoolbox extension.

Viral Infection and Electrophysiology

A Sprague Dawley (SD) rat was intravitreally injected with 3 μl of an AAV2-CAG-Chop2/GFP-WPRE-BGH-polyA expression vector at a concentration of $1.2\times10^{11}$ genomic particles/ml (GeneDetect Ltd).

The animal was sacrificed a month and a half post viral infection. The transfected retina was isolated in physiological solution and mounted on a transparent multi-electrode array (MEA, Multi Channel Systems MCS Gmbh) with the fluorescent ganglion cells facing the electrodes. The inter-electrode spacing was 200 μm with 30 μm electrode diameter for the total MEA area of 1.6 mm by 1.6 mm. The image was projected onto the retina from below through a ×4 microscope objective. The retina was stimulated with vertical blue bars projected by the SLM. Each bar was generated by random projection of 20 spots with intensity 0.1 $mW/mm^2$ updated every 0.5 ms. The spot size was 12 μm at FWHM. Each bar scans the entire field of view within 1.13 seconds, moving from right to left. The stimulus was presented multiple times, once in 10 seconds.

FIG. 11A shows raw data of a single neuron response, as a function of the time in seconds. As shown, there are numerous response events above the background noise level, demonstrating the ability of the spatially modulated light of the present embodiments to stimulate the neuron.

FIG. 11B shows responses of three different neurons for multiple trials of bar presentation (scale bar: 1 second). Each vertical line represents a single stimulation of the respective cell. As shown, the stimulations of each cell are consistent, namely the neuron is repeatedly stimulated at equivalent time instants within a trial. On the other hand, the stimulation events of different neurons occur at different time instants within scan cycle of the bar over the hologram. Thus, different regions over the hologram address different neurons. This demonstrates the ability of the spatially modulated light of the present embodiments to generate patterned stimulation.

Example 2

In this Example, the thermal response of tissue was investigated by computer simulations. The simulations were conducted using COMSOL® simulation software (Massachusetts, USA).

The simulations were directed to the investigation of the time-dependence of the response of small volume of tissue to heating via optical energy. The tissue was simulated as made of water.

FIGS. 12A-D show spatial (FIGS. 12A-C) and temporal (FIG. 12D) thermal response profile of a tissue of about (30 μm)$^3$, following heating by a 0.5 ms pulse of light. Spatial profiles are shown at t=0.5 ms (FIG. 12A), 2 ms (FIG. 12B) and 4 ms (FIG. 12C), where t=0 corresponds to pulse onset. The light was simulated as being focused onto a diameter of 30 μm absorbed within a 30 μm depth in the tissue. The energy dissipation per unit area was 63 mJ/cm$^2$.

As shown a temperature spike has been successfully obtained at the target location, demonstrating the ability of the present embodiments to induce thermal transients in tissue. The temperature was increased during the light pulse reaching a maximum of about 4° C. at t=0.5 ms. The drop of temperature was exponential with a drop of about 3° C. within the first 5 milliseconds.

Example 3

In this Example, the ability to inject a light absorbing medium next to or into the retina in vivo was demonstrated.

An Albino SD rat (300 gr) was anesthetised and 5 μl of India ink were injected intravitrealy into the eyeball in-vivo. The animal was sacrificed 20 min later and the eyeball was enucleated and placed in 4% paraformaldehyde for fixation and slicing.

FIG. 13 is an image of a 20 μm thick slice of the retina. Shown in FIG. 13 are the photoreceptors, the inner retina with the retinal ganglion cells and the India ink stain.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of stimulating neurons, the method comprising:

generating a stimulation light pattern; and using optics characterized by a numerical aperture selected such that an elementary spot size of said stimulation light pattern is at most 20 microns for directing said stimulation light pattern to a light absorbing medium implanted extracellularly at a target location having the neurons therein, wherein wavelengths and intensities of said light are selected so as to heat said light absorbing medium by light absorption, said heating being sufficient to stimulate neurons nearby said light absorbing medium.

2. The method of claim 1, further comprising extracellularly implanting said light absorbing medium at said target location.

3. The method of claim 1, wherein said directing of said light is done so as to simultaneously form a stimulation pattern at said target location.

4. The method of claim 3, further comprising spatially modulating said light so as to encode said stimulation pattern therein.

5. A method of stimulating neurons, comprising:

spatially modulating light so as to encode a stimulation pattern therein; and using optics characterized by a numerical aperture selected such that an elementary spot size of said stimulation pattern is at most 20 microns for directing said light to a target location having the neurons therein so as to simultaneously form said stimulation pattern at said target location, wherein wavelengths and intensities forming said stimulation pattern are selected so as to selectively stimulate said neurons.

6. A neurostimulation system, comprising:

a light absorbing medium implantable extracellularly in a living body at target location having therein a plurality of neurons;

an illumination system having a light source for generating stimulation light pattern; and optics characterized by a numerical aperture selected such that an elementary spot size of said stimulation light pattern is at most 20 microns, and being for directing said light to said light absorbing medium, wherein wavelengths and intensities of said light are selected so as to heat said light absorbing medium by light absorption, said heating being sufficient to stimulate neurons nearby said light absorbing medium.

7. The system of claim 6, wherein said illumination system comprises a projector system configured for generating a spatially modulated light beam encoded with a stimulation pattern.

8. A neurostimulation device, comprising:

a projector system for generating a spatially modulated light beam encoded with a stimulation pattern; and optics characterized by a numerical aperture selected such that an elementary spot size of said stimulation pattern is at most 20 microns, and being configured for directing said light to a target location having a plurality of neurons so as to simultaneously form said stimulation pattern at said target location;

wherein wavelengths and intensities forming said stimulation pattern are selected so as to selectively stimulate said neurons.

9. A neuroprosthesis system, comprising:

the neurostimulation device of claim 8; and a sensing device for sensing information from the environment and transmitting signals pertaining to said information to said neurostimulation device;

wherein said projector system is configured for calculating said stimulation pattern based on said information.

10. The method of claim 5, wherein said target location is implanted with a light absorbing medium, and wherein said wavelengths and intensities are selected so as to heat said light absorbing medium by light absorption, said heating being sufficient to stimulate neurons nearby said light absorbing medium.

11. The method of claim 5, wherein said neurons express a light-activated ion channel protein, and wherein said wavelengths and intensities are selected so as to activate said light-activated ion channel protein.

12. The method of claim 11, further comprising transfecting said neurons by gene transfer vectors capable of inducing expression of said light-activated ion channel protein.

13. The system of claim 7, wherein said projector system comprises a spatial light modulator having a liquid crystal.

14. The system of claim 7, wherein said projector system is configured for providing phase-only modulation.

15. The system of claim 7, wherein said projector system is configured for providing concurrent phase and amplitude modulation.

16. The system of claim 7, wherein said optics is a free-space optics.

17. The system of claim 7, wherein said optics comprises an optical fiber bundle.

18. The method of claim 1, wherein said light absorbing medium is extracellularly distributed at said target location.

19. The method of claim 1, wherein said light absorbing medium comprises light absorbing particles.

20. The method of claim 1, wherein said light absorbing medium comprises a dye.

21. The method of claim 19, wherein said light absorbing particles are metallic nanoparticles.

22. The method of claim 1, wherein said light absorbing medium comprises a light absorbing film.

23. The method of claim 3, wherein said stimulation pattern is a three-dimensional stimulation pattern.

24. The method of claim 1, wherein said light is selected so as to generate non-linear optical effects.

25. The method of claim 24, wherein said light is characterized by a pulse width which is shorter that one picosecond.

26. The method of claim 1, wherein said target location is a retina present in a living body.

27. The method of claim 1, wherein said target location is a cochlea present in a living body.

28. The method of claim 1, wherein said target location is in a cerebral cortex present in a living body.

29. The method of claim 1, wherein said target location is in the brainstem present in a living body.

30. The method of claim 1, wherein said target location is the vagus nerve present in a living body.

31. The method of claim 1, wherein said target location is a cranial nerve present in a living body.

32. The method of claim 1, wherein said target location is a neuron culture.

33. The device of claim 8, wherein said modulated light beam is dynamically encoded with an alternating sequence of pseudo-random frames forming together a symmetric stimulation pattern at said target location.

34. The device of claim 8, wherein said intensities are selected so as to reduce efficiency inhomogeneities within said stimulation pattern.

35. The device of claim 34, wherein said intensities are inversely proportional to a square of a sinc function.

36. The device of claim 8, wherein said light is encoded in a time-multiplexed manner, wherein stimulation patterns transmitted at different times correspond to different light spectra.

37. The system of claim 7, wherein said optics comprises an optical fiber.

38. The method of claim 1, wherein said optics comprises an optical fiber.

39. The method of claim 1, wherein said optics comprises an optical fiber bundle.

40. The method of claim 5, wherein said optics comprises an optical fiber.

41. The method of claim 5, wherein said optics comprises an optical fiber bundle.

42. The device of claim 8, wherein said optics comprises an optical fiber.

43. The device of claim 8, wherein said optics comprises an optical fiber bundle.

44. A neurostimulation device, comprising:

a projector system for generating a spatially modulated light beam encoded with a stimulation pattern in a time-multiplexed manner, and optics configured for directing said light to a target location having a plurality of neurons so as to simultaneously form said stimulation pattern at said target location;

wherein wavelengths and intensities forming said stimulation pattern are selected so as to selectively stimulate said neurons, and wherein stimulation patterns transmitted at different times correspond to different light spectra.

45. A neurostimulation device, comprising:

a projector system for generating a spatially modulated light beam encoded with a stimulation pattern; and optics configured for directing said light to a target location having a plurality of neurons so as to simultaneously form said stimulation pattern at said target location;

wherein wavelengths and intensities forming said stimulation pattern are selected so as to selectively stimulate said neurons, and wherein said intensities are selected so as to reduce efficiency inhomogeneities within said stimulation pattern.

* * * * *